(12) United States Patent
Takasaki et al.

(10) Patent No.: US 6,316,670 B1
(45) Date of Patent: Nov. 13, 2001

(54) POLYHALOGENOMETHYLSULFONYL COMPOUND

(75) Inventors: Masaru Takasaki; Katsuyuki Watanabe; Hisashi Okamura, all of Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/618,449

(22) Filed: Jul. 18, 2000

(30) Foreign Application Priority Data

Jul. 19, 1999 (JP) .................................................. 11-205329

(51) Int. Cl.$^7$ ................................................ C07C 233/65
(52) U.S. Cl. ................................................................ 564/162
(58) Field of Search .............................................. 564/162

(56) References Cited

U.S. PATENT DOCUMENTS

| | | |
|---|---|---|
| 3,874,946 | 4/1975 | Costa et al. . |
| 3,955,982 | 5/1976 | VanAllan et al. . |
| 4,452,885 | 6/1984 | Nozawa et al. . |
| 4,546,075 | 10/1985 | Kitaguchi et al. . |
| 4,756,999 | 7/1988 | Swain et al. . |

FOREIGN PATENT DOCUMENTS

| | | |
|---|---|---|
| A10605981 | 7/1994 | (EP) . |
| A10631176 | 12/1994 | (JP) . |
| A09258367 | 10/1997 | (JP) . |
| A09265150 | 10/1997 | (JP) . |
| A10197989 | 7/1998 | (JP) . |

*Primary Examiner*—Shailendra Kumar
(74) *Attorney, Agent, or Firm*—Birch, Stewart, Kolasch & Birch, LLP

(57) ABSTRACT

The object of the present invention is to provides a novel polyhalogenomethylsulfonyl compound which can be used for providing a thermally processed image recording material which has a high sensitivity, gives less fog, and has a good stock stability and a good image storage stability of dark and high temperature or light storage. According to the present invention, there is provided a polyhalogenomethylsulfonyl compound represented by the following formula (1), or salts thereof, or hydrates or solvates thereof:

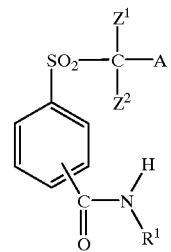

(1)

wherein $Z^1$ and $Z^2$ each independently represents a halogen atom; A represents a hydrogen atom or a halogen atom; and $R^1$ represents an alkyl group having from 2 to 12 carbon atoms, which may have one or more substituents, an alkenyl group having from 2 to 12 carbon atoms, which may have one or more substituents, or an alkinyl group having from 2 to 12 carbon atoms, which may have one or more substituents.

8 Claims, 1 Drawing Sheet

POLYHALOGENOMETHYLSULFONYL COMPOUND

FIELD OF THE INVENTION

The present invention relates to a polyhalogenomethylsulfonyl compound. More specifically, the present invention relates to a polyhalogenomethylsulfonyl compound which can be used as a component for a thermally processed image recording material which has a high sensitivity, gives very less fog, and is excellent in the stock stability and the image stability after development, and also which can be used as a radical polymerization initiator.

BACKGROUND OF THE INVENTION

A large number of photosensitive materials are known which have a photosensitive layer on a support and form image by imaging exposure. An example of a system that enables environmental conservation or simplification of image formation includes a technique of forming an image by heat development.

In recent years, reduction of amount of waste processing solutions is strongly desired in the medical diagnosis field and the photographic art field from the standpoints of environmental protection and space savings. Techniques relating to photothermographic materials for use in the medical diagnosis field and the photographic art field are required which enables efficient exposure by a laser scanner or a laser image setter and formation of a clear black image having high resolution and sharpness. These photothermographic materials can provide users with a simple and non-polluting heat development processing system which eliminates the use of solution-type processing chemicals.

Methods for forming an image by heat development are described, for example, in U.S. Pat. Nos. 3,152,904 and 3,457,075 and D. Klosterboer, Imaging Processes and Materials, "Thermally Processed Silver Systems", Neblette, 8th ed., compiled by J. Sturge, V. Walworth and A. Shepp, Chapter 9, p.279, (1989). These photothermographic material contain a reducible light-insensitive silver source (e.g., organic silver salt), a photocatalyst (e.g., silver halide) in a catalytically active amount, and a reducing agent for silver, which are usually dispersed in an organic binder matrix. This photothermographic material is stable at an ambient temperature, but when the material is heated at a high temperature (e.g., 80° C. or higher) after light exposure, silver is produced through an oxidation-reduction reaction between the reducible silver source (which functions as an oxidizing agent) and the reducing agent. The oxidation-reduction reaction is accelerated by catalytic action of a latent image generated upon exposure. The silver produced by the reaction of the reducible silver salt in the exposure region provides a black image and this presents a contrast to the non-exposure region to form an image.

In the thermally processed photographic materials, which contains the photothermographic material and the thermographic material, the formation of fog is a large problem. Many attempts have been made for reducing fog of the thermally processed photographic materials, and for example, U.S. Pat. No. 3,589,903 discloses mercury salt. In other examples, U.S. Pat. No. 4,152,160 discloses carboxylic acids such as benzoic acid and phthalic acid, U.S. Pat. No. 4,784,939 discloses benzoylbenzoic acid compounds, U.S. Pat. No. 4,569,906 discloses indane and tetralinecarboxylic acid, U.S. Pat. No. 4,820,617 discloses dicarboxylic acids, and U.S. Pat. No. 4,626,500 discloses heteroaromatic carboxylic acids. U.S. Pat. Nos. 4,546,075, 4,756,999, 4,452,885, 3,874,946 and 3,955,982 disclose halogenated compounds. Furthermore, U.S. Pat. No. 5,028,523, discloses halogen molecules and a halogen atom bonded to a heteroatom ring. U.S. Pat. No. 4,103,312 and British Patent 1,502,670 disclose palladium compounds, U.S. Pat. No. 4,128,428 discloses iron family metals, U.S. Pat. Nos. 4,123,374, 4,129,557, and 4,125,430 disclose substituted triazoles, U.S. Pat. Nos. 4,213,784 and 4,245,033 and Japanese Patent Laid-Open No. 26019/1976 disclose sulfur compounds, U.S. Pat. No. 4,002,479 discloses thiouracils, Japanese Patent Laid-Open No. 123331/1975 discloses sulfinic acid, U.S. Pat. Nos. 4,125,403, 4,152,160 and 4,307,187 disclose the metal salts of thiosulfonic acid, Japanese Patent Laid-Open Nos. 20923/1978 and 19825/1978 disclose the combinations of metal salts of thiosulfonic acid and sulfinic acid, and Japanese Patent Publication No. 50810/1987 and Japanese Patent Laid-Open Nos. 209797/1995 and 43760/1997 disclose thiosulfonic acid esters.

Japanese Patent Laid-Open No. 42529/1976 and Japanese Patent Publication No. 37368/1988 disclose disulfide compounds. However, these compounds have the faults that the effect of preventing the formation of fog is low and when the addition amount is increased, Dmax (the maximum density) and the sensitivity are lowered.

Furthermore, in the photothermographic materials, polyhalogen compounds are very effective components as antifoggants and storage stabilizers, and are disclosed, for example, in Japanese Patent Publication No 165/1979, EP-605981A, EP-631176A, and U.S. Pat. Nos. 4,546,075, 4,756,999, 4,452,885, 3,874,946, and 3,955,982. However, the compounds described therein have the problems that the effect of preventing the formation of fog is insufficient, the storage stability of the photothermographic materials before development is insufficient, and the image storage stability (e.g., coloring of non-imaged portions by heat or light) after heat development is insufficient, and also have the problems that when the compounds is added in such an amount that sufficiently prevents the formation of fog, the sensitivity is lowered and Dmax is lowered.

SUMMARY OF THE INVENTION

The present invention has been made for solving the above-mentioned problems of the techniques of the related art. The object of the present invention is to provides a novel polyhalogenomethylsulfonyl compound which can be used for providing a thermally processed image recording material which has a high sensitivity, gives less fog, and has a good stock stability and a good image storage stability of dark and high temperature or light storage.

As the result of making various study for solving the above-described problems, the present inventors have found that when the specific polyhalogenomethylsulfonyl compounds of the invention represented by following formula (1) is used for a thermally processed image recording material, an excellent thermally processed image recording material can be obtained which gives the desired effects, and have succeeded in accomplishing the present invention.

According to the present invention, there is provided a polyhalogenomethylsulfonyl compound represented by the following formula (1), or salts thereof, or hydrates or solvates thereof:

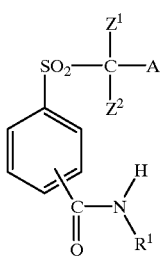

(1)

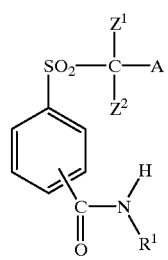

(1)

wherein $Z^1$ and $Z^2$ each independently represents a halogen atom; A represents a hydrogen atom or a halogen atom; and $R^1$ represents an alkyl group having from 2 to 12 carbon atoms, which may have one or more substituents, an alkenyl group having from 2 to 12 carbon atoms, which may have one or more substituents, or an alkinyl group having from 2 to 12 carbon atoms, which may have one or more substituents.

Preferably, $R^1$ is an unsubstituted alkyl group having from 2 to 12 carbon atoms, an unsubstituted alkenyl group having from 2 to 12 carbon atoms, or an unsubstituted alkinyl group having from 2 to 12 carbon atoms.

More preferably, $R^1$ is an unsubstituted alkyl group having from 3 to 5 carbon atoms, an unsubstituted alkenyl group having from 3 to 5 carbon atoms, or an unsubstituted alkinyl group having from 3 to 5 carbon atoms.

The alkyl group, the alkenyl group, or the alkinyl group represented by $R^1$ may have one or more substituents and the preferred substituent is one or more substituents selected from the group consisting of a halogen atom; an alkoxy group; a nitro group; an amino group which may be substituted by an alkyl group; an alkoxycarbonyl group; an acylthio group; a silyl group; an alkylthio group; and a heterocyclic group.

Preferably, $Z^1$ and $Z^2$ each is a bromine atom and A is a hydrogen atom or a bromine atom.

Preferably, —$CONHR^1$ exists at the meta-position to —$SO_2C(Z^1)(Z^2)A$.

According to another aspect of the present invention, there is provided a thermally processed image recording material wherein the polyhalogenomethylsulfonyl compound or salts thereof, or hydrates or solvates thereof of claim 1 is used.

DETAILED DESCRIPTION OF THE INVENTION

Figure 1:
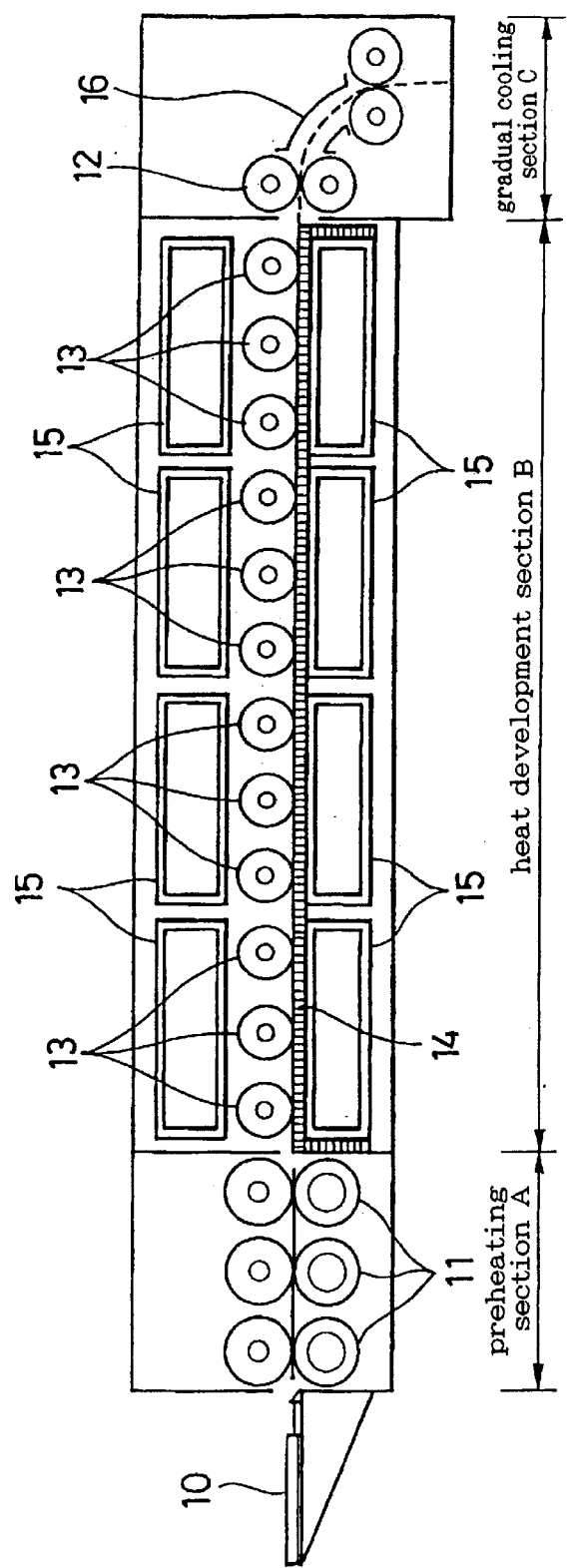
FIG. 1 is a side view showing the construction of a heat development apparatus used in the Examples. In the FIGURE, there are shown a thermally processed image recording material 10, carrying-in roller pairs 11, carrying-out roller pairs 12, rollers 13, a flat surface 14, heaters 15, and guide panels 16. The apparatus consists of a preheating section A, a heat development section B, and a gradual cooling section C.

The present invention is described in detail in connection with its various embodiments and the methods of carrying out the invention.

The polyhalogenomethylsulfonyl compound of the invention is represented by the following formula (1).

In the formula (1), $Z^1$ and $Z^2$ each independently represents a halogen atom, which may be fluorine, chlorine, bromine or iodine. Most preferably, both of $Z^1$ and $Z^2$ are a bromine atom.

In the formula (1), A represents a hydrogen atom or a halogen atom, which may be fluorine, chlorine, bromine or iodine. A is preferably a halogen atom and is particularly preferably a bromine atom.

In the formula (1), it is most preferred that all of $Z^1$, $Z^2$, and A are atom.

In the formula (1), $R^1$ represents an alkyl group having from 2 to 12 carbon atoms, which may have one or more substituents, an alkenyl group having from 2 to 12 carbon atoms, which may have one or more substituents, or an alkinyl group having from 2 to 12 carbon atoms, which may have one or more substituents. The alkyl group, the alkenyl group, or the alkinyl group may have a straight chain, a branched chain, a cyclic chain, or the combination thereof.

The straight chain or branched alkyl group having from 2 to 12 carbon atoms includes, for example, ethyl, n-propyl, isopropyl, n-butyl, isobutyl, sec-butyl, tert-butyl, n-pentyl, isopentyl, hexyl, heptyl, octyl, nonyl, decyl, undecyl, and dodecyl. The cyclic alkyl group having from 2 to 12 carbon atoms includes cyclopropyl, cyclobutyl, cyclopentyl, cyclohexyl, cycloheptyl, cyclooctyl, cyclononyl, cyclodecyl, cycloundecyl, cyclododecyl, etc. Examples of the alkenyl group or the alkinyl group having from 2 to 12 carbon atoms include those which are obtained by replacing at least one carbon-carbon single bond of each of the alkyl groups described above with a double bond and/or a triple bond.

Preferred examples of the alkyl group include isopropyl, n-butyl, cyclopentyl, etc., preferred examples of the alkenyl group include allyl, 2-butenyl, etc., and preferred examples of the alkinyl group include propargyl, 2-butynyl, etc.

In the formula (1), the alkyl group, the alkenyl group or the alkinyl group represented by $R^1$ may have one or more substituents as described above. The substituent preferably has not more than 3 carbon atoms and π value (π value defined in "Journal of Medical Chemistry", 1973, 1207) of at least −0.3. Examples of the substituent include a halogen atom (e.g., fluorine, chlorine, bromine, etc.), an alkoxy group (e.g., methoxy, ethoxy, etc.), a nitro group, an amino group which may be substituted by an alkyl group (e.g., dimethylamino, etc.), an alkoxycarbonyl group (e.g., methoxycarbonyl, ethoxycarbonyl, etc.), an acylthio group (e.g., acetylthio, etc.), a silyl group, an alkylthio group (e.g., methylthio, ethylthio, etc.), a heterocyclic group [e.g., a monocyclic, bicyclic, or tricyclic heterocyclic group containing one or more hetero atoms (nitrogen, oxygen, sulfur, etc.) as the ring-constituting atoms, which may be an alicyclic group or an aromatic group and where one or more rings included in the heterocyclic group may be partially or completely saturated. Examples thereof include imidazolyl, triazolyl, tetrazolyl, thiadiazolyl, thiazolyl, oxazolyl, etc.], etc. The preferred substituent is a halogen atom or an alkoxy group. When two or more substituents exist, these substituents may be the same or different.

$R^1$ is preferably an unsubstituted alkyl group, an unsubstituted alkenyl group, or an unsubstituted alkinyl group.

In the formula (1), $R^1$ is preferably an unsubstituted alkyl group having from 3 to 5 carbon atoms or an unsubstituted alkenyl group having from 3 to 5 carbon atoms, and particularly preferably an unsubstituted alkyl group having from 4 or 5 atoms.

In the formula (1), $-SO_2-C(Z^1)(Z^2)(A)$ and $-CONHR^1$ may be ortho-substituted, meta-substituted, or para-substituted with each other, and is most preferably meta-substituted with each other.

The compounds of the formula (1) wherein all of $Z^1$, $Z^2$, and A are a bromine atom, and $-SO_2-C(Z^1)(Z^2)(A)$ and $-CONHR^1$ are meta-substituted with each other, are one of the most preferred embodiments of the invention.

The compound of the invention represented by the formula (1) may form an acid addition salt and the acid addition salt is included in the scope of the invention. Examples of the acid addition salt include mineral acid salts such as hydrochloride, hydrobromides, nitrates, sulfates, and phosphates, as well as organic acid salts such as p-toluenesulfonates, methanesulfonates, oxalates, tartrates, malates, citrates, etc. Depending on the type of the substituent, the compound of the invention may form a base addition salt. Furthermore, the compound of the invention may exist as hydrate or solvate. All of the salts, the hydrates and the solvates are included in the scope of the invention.

Depending on the type of the substituent, the compound of the invention may have one or more asymmetric carbon atoms. In such a case, there may exist stereoisomers such as an optical isomer having one or more asymmetric carbon atoms and a diastereoisomer having two or more asymmetric carbon atoms. Any stereoisomer of a pure form, any mixture of the stereoisomers, and racemic forms and the like are all included in the scope of the invention.

When, in the formula (1), $R^1$ represents an alkenyl group which may have a substituent, due to the double bond existing in the alkenyl group, a geometric isomer may exist. Any geometric isomer of a pure form and any mixture of the geometric isomers are all included in the scope of the invention.

Specific examples of the compound of the formula (1) are shown below, but the present invention is not limited to them.

D-1 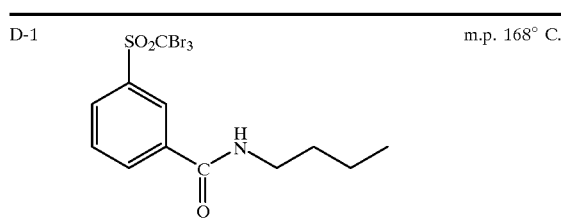 m.p. 168° C.

D-2 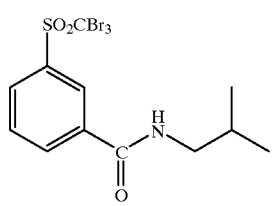 m.p. 114° C.

D-3 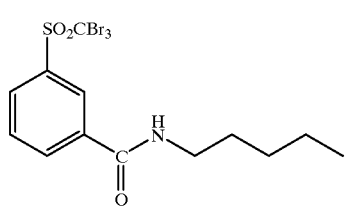 m.p. 144° C.

D-4 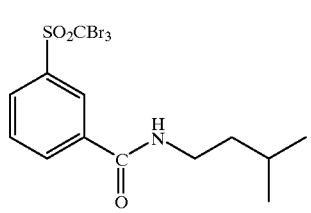 m.p. 179° C.

D-5 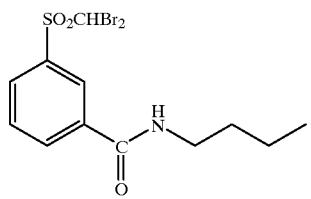 m.p. 101° C.

D-6 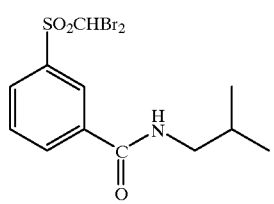

D-7 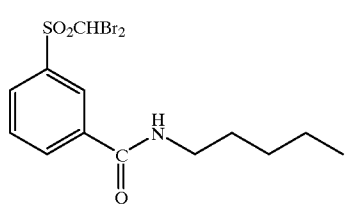

D-8 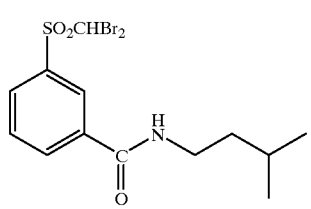

-continued
D-9 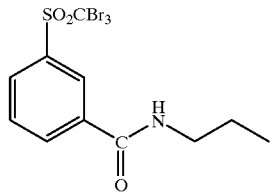 m.p. 187° C.
D-10 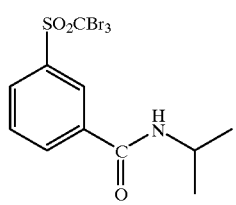 m.p. 152° C.
D-11 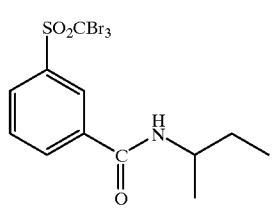
D-12 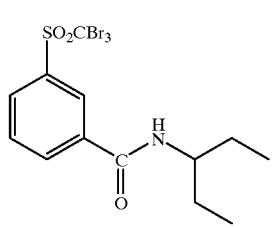 m.p. 139° C.
D-13 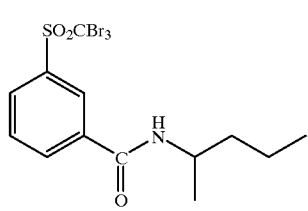 m.p. 137° C.
D-14 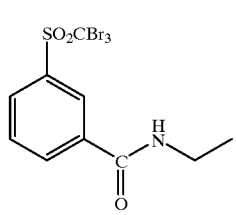
D-15 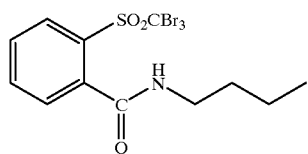
D-16 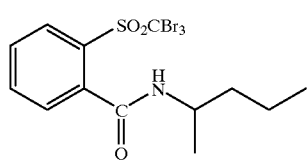
-continued
D-17 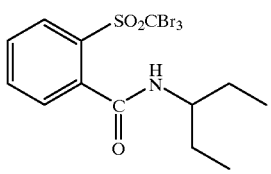 m.p. 188° C.
D-18 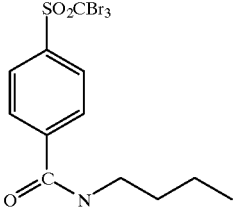
D-19 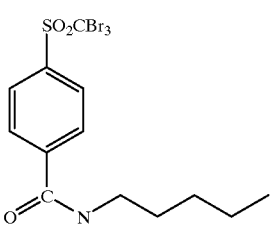
D-20 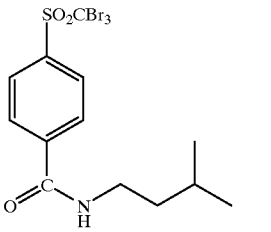
D-21 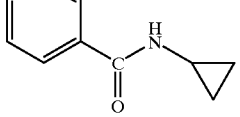
D-22 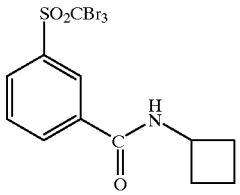
D-23 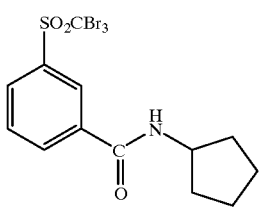 m.p. 192° C.

| | | |
|---|---|---|
| D-24 | SO₂CBr₃ with benzene ring, meta CONH-allyl | m.p. 156° C. |
| D-25 | SO₂CBr₃ with benzene ring, meta CONH-propargyl | m.p. 168° C. |

The general Synthesis examples of the tribromomethanesulfonyl compound and the dibromomethanesulfonyl compound, wherein the benzene ring is substituted with a carbamoyl group at its meta position, each of which is one of the particularly preferred embodiments of the invention, are shown below.

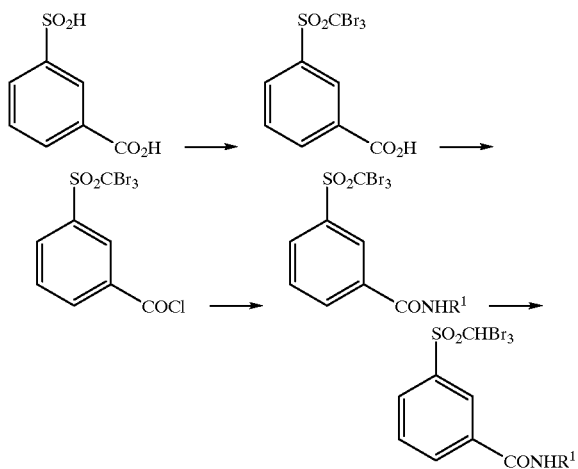

(Step 1) General synthesis method of 3-tribromomethanesulfonylbenzoic acid (B) from 3-sulfinobenzoic acid (A):

In water are dissolved easily available sulfinobenzoic acid (1 equivalent), sodium hydroxide (2 equivalents), sodium chloroacetate (2 equivalents), and sodium bromide (0.05 equivalent), and after stirring the solution at a temperature of 50 to 80° C. for 3 to 9 hours, the temperature of the reaction mixture is lowered to room temperature [the reaction mixture (1)].

On the other hand, sodium hydroxide (7.35 equivalents) is dissolved in water and while keeping the solution at a temperature of 10° C. or lower, bromine (3.5 equivalents) is gradually added dropwise to the solution. To the thus obtained aqueous solution of NaOBr is gradually added dropwise the reaction mixture (1). In this case, care is taken so that the reaction temperature does not exceed 20° C. After stirring the mixture at 20° C. for one hour, the reaction mixture is poured into an aqueous solution of 2 mol/L hydrochloric acid to precipitate crude crystals. The crude crystals are recovered by filtration, sufficiently washed with water, dried, and washed with acetonitrile followed by drying to obtain 3-tribromomethanesulfonylbenzoic acid (B) as white crystals.

(Step 2) General synthesis method of 3-tribromomethanesulfonyl benzoylchloride (C):

To 3-tribromomethanesulfonylbenzoic acid (B) obtained in the above-described (Step 1) are added dimethylformamide and thionyl chloride and the mixture is refluxed for one hour. The reaction mixture is filtered, and hexane is added to the filtrate to deposit crystals. The crystals are recovered by filtration and dried to obtain 3-tribromomethanesulfonyl benzoylchloride (C) as white crystals.

(Step 3) General synthesis method of the tribromomethanesulfonyl compound of the invention:

The amine compound (3 equivalents) represented by the formula $NH_2R^1$ wherein $R^1$ is the same as defined above in regard to the formula (1), is dissolved in 20 ml of an alcohol (methanol, ethanol, isopropyl alcohol, etc.) or dimethylacetamide in an ice bath, and 3-tribromomethanesulfonyl benzoylchloride (C) (1 equivalent) synthesized in above-described Step 2 is gradually added to the solution. The mixture is stirred at room temperature for 1 to 5 hours and then a neutralizing amount of an aqueous solution of hydrochloric acid is added to the reaction mixture to deposit crystals. The crystals are recovered by filtration, sufficiently washed with water, and dried to obtain the tribromomethanesulfonyl compound of the invention.

(Step 4) General synthesis method of the dibromomethanesulfonyl compound of the invention:

To a tribromomethanesulfonyl compound (1 equivalent) and sodium sulfite (3 equivalents) are added methylene chloride and water, and the reaction mixture is stirred at room temperature for 2 hours. The reaction mixture is extracted with methylene chloride, and the extract is washed twice with water and dried over magnesium sulfate. The solvent is removed to obtain a dibromomethanesulfonyl compound.

In the formula (1), $Z^1$ and $Z^2$ each independently represents a halogen atom and A represents a hydrogen atom or a halogen atom. When $Z^1$, $Z^2$, and A represent other halogen atom than a bromine atom, in the above-described (Step 1) a desired other halogen atom may be used in place of bromine.

In the formula (1), $R^1$ represents an alkyl group having from 2 to 12 carbon atoms, which may have one or more substituents, an alkenyl group having from 2 to 12 carbon atoms, which may have one or more substituents, or an alkinyl group having from 2 to 12 carbon atoms, which may have one or more substituents. In order to synthesize the compound having a desired $R^1$, the above-described Step 3 may be carried out using the amine compound having the corresponding $R^1$.

In the formula (1), the group represented by $—CONHR^1$ may exist at any position selected from the 2-position (ortho-position), the 3-position (meta-position), and the 4-position (para-position) to $—SO_2C(Z^1)(Z^2)A$ on the benzene ring. In order to obtain the compound having $—CONHR^1$ at the 2-position or the 4-position, 2-sulfinobenzoic acid or 4-sulfinobenzoic acid may be used as the starting material in place of 3-sulfinobenzoic acid.

The compound of the invention represented by the formula (1) can be used in a thermally processed image recording material. In this case, the compound of the formula (1) may be used as a solution dissolved in water or a suitable organic solvent such as, for example, alcohols (e.g., methanol, ethanol, propanol, and a fluorinated alcohol), ketones (e.g., acetone, methyl ethyl ketone and methyl isobutyl ketone), dimethylformamide, dimethyl sulfoxide, methyl cellosolve, etc. The compound having an acidic group bonded thereto may be neutralized with an equivalent of an alkali, and be used as a salt thereof.

Alternatively, the compound of the present invention may be dissolved by using an oil such as dibutyl phthalate, tricresyl phosphate, glyceryl triacetate, or diethyl phthalate, or an auxiliary solvent such as ethyl acetate or cyclohexane. An emulsified dispersion of the compound may be mechanically prepared by an emulsion dispersing method well-known in the art, and can be used in the thermally processed image recording material. The powder of the compound is dispersed in water by means of a method which is known as a solid-dispersing method, using a ball mill, a colloid mill, a sand grinder mill, manton gaulin, a microfluidizer, or ultrasonic wave, and the dispersion may be used in the thermally processed image recording material.

The type of the thermally processed image recording material for which the compound of the invention represented by the formula (1) can be used is not particularly limited, but it is preferred that the thermally processed image recording material has an image-forming layer containing an organic silver salt as a reducible silver salt and a binder on a support, and a layer on the image-forming layer side contains a reducing agent as well as a photosensitive silver halide. It is also preferred that the image-forming layer is a photosensitive layer containing a photosensitive silver halide. For example, European Patent Publication (EP) 0803764A1 can be referred to.

In the case of using the compound of the invention represented by the formula (1) for a thermally processed image recording material, it is preferred that a layer on the image-forming layer side to the support contains the compound represented by the formula (1). The compound represented by the formula (1) may be contained in the image-forming layer or in other layer on the image-forming layer side. It is particularly preferred that the compound of the invention is contained in the image-forming layer or a layer adjacent to the image-forming layer.

When a thermally processed image recording material prepared by using the compound represented by the formula (1) is compared with that prepared by using other polyhalogenated compound than the compound of the formula (1), the thermally processed image recording material has a high sensitivity, and the formation of heat fog at non-imaged portions is restrained and the heat/light storage stability of images can be increased.

When the compound of the invention represented by the formula (1) is used for a thermally processed image recording material, it is added in an amount of $1\times10^{-6}$ to 1 mole, preferably $1\times10^{-5}$ to $5\times10^{-1}$, and more preferably $2\times10^{-5}$ to $2\times10^{-1}$ mole per mole of silver in a thermally processed image recording material.

The thermally processed image recording material for which the compound of the invention represented by the formula (1) can be used, is further described below in detail.

The thermally processed image recording material preferably has an image-forming layer containing an organic silver salt as a reducible silver salt and a reducing agent for silver ion, both of which are dispersed in a matrix of binder. A catalytically active amount of photocatalyst (preferably, a photosensitive silver halide) may be used for preparing photosensitive material. If necessary., color-tone adjustor may be used for controlling the color-tone of silver.

The organic silver salt which can be used in the present invention is relatively stable against light, but forms a silver image when it is heated at 80° C. or higher in the presence of an exposed photocatalyst (e.g., a latent image of photosensitive silver halide) and a reducing agent. The organic silver salt may be any organic substance containing a source capable of reducing the silver ion. Such non-photosensitive organic silver salts are disclosed in Japanese Patent Laid-open 62899/1998, paragraphs 0048–0049; European Patent Publication 0803764A1, page 18, line 24 to page 19, line 37; European Patent Publication 0962812A1; Japanese Patent Laid-open 349591/1999; Japanese Patent Laid-open 7683/2000; Japanese Patent Laid-open 72711/2000 and the like. A silver salt of an organic acid, particularly a silver salt of a long chained aliphatic carboxylic acid (having from 10 to 30, preferably from 15 to 28 carbon atoms) is preferred. Examples of preferred organic silver salt include silver behenate, silver arachidinate, silver stearate, silver oleate, silver laurate, silver caproate, silver myristate, silver palmitate, and a mixture thereof. Among them, organic silver salt containing silver behenate in an amount of 75 mol % or more is preferably used.

The organic silver salt may be used in any desired amount, and it is preferably used in an amount of 0.1 to 5 g/m², more preferably 1 to 3 g/m², in terms of silver amount.

The reducing agent for silver ion may be any substance, preferably an organic substance, which reduces the silver ion to metal silver. Such reducing agents are disclosed in Japanese Patent Laid-open 65021/1999, paragraph 0043–0045; and European Patent Publication 0803764A1, page 7, line 34 to page 18, line 12.

The reducing agent is added preferably in an amount of 0.01 to 5.0 g/m², more preferably 0.1 to 3.0 g/m², and is added in an amount of 5 to 50 mol %, more preferably 10 to 40 mol % based on per mole of silver on the surface having an image-forming layer. The reducing agent is preferably contained in an image recording layer.

The photosensitive silver halide for use in the present invention is not particularly limited as for the halogen composition, and silver chloride, silver chlorobromide, silver bromide, silver iodobromide, and silver chloroiodobromide may be used. The halide composition may have a uniform distribution in the grains, or the compositions may change stepwise or continuously in the grains. Silver halide grains having a core/shell structure may be preferably used.

The methods for the preparation of the photosensitive silver halide are well known in the art, and for example, the methods described in Research Disclosure, No. 17029 (June, 1978) and U.S. Pat. No. 3,700,458, can be used.

The photosensitive silver halide may be added preferably in an amount of 0.03–0.6 g/m², more preferably 0.05–0.4 g/m², still more preferably 0.1–0.4 g/m², as represented by the amount of silver per 1 m² of photosensitive material.

The binder in the organic silver salt containing layer may be any polymer. Preferred binders are transparent or semi-transparent., and are generally colorless. The binders may be polymer or copolymer of natural resin, polymer or copolymer of synthetic resin, or other material capable of forming films such as gelatin, gum, poly(vinyl alcohol), hydroxyethyl cellulose, cellulose acetate, cellulose acetate butyrate, poly(vinyl pyrrolidone), casein, starch, poly(acrylic acid), poly(methyl methacrylate), poly(vinyl chloride), poly (methacrylic acid), styrene-maleic anhydride copolymer, styrene-acrylonitrile copolymer, styrene-butadiene copolymer, poly(vinyl acetals) (e.g., poly(vinyl formal), poly(vinyl butyral)), poly(esters), poly(urethanes), phenoxy resin, poly(vinylidene chloride), poly(epoxides), poly(carbonates), poly(vinyl acetate), polyolefin, cellulose esters and poly(amides). The binder may be coated and formed after being dissolved in water or an organic solvent or in the form of an emulsion.

The total amount of the binder in the image forming layer is preferably 0.2–30 g/m$^2$, more preferably 1–15 g/m$^2$.

Other components and constitutions which may be applied for the thermally processed image recording material for which the compound of the invention represented by the formula (1) can be used, may be selected with referring to Japanese Patent Laid-open 62899/1998, European Patent Publication 0803764A1, 0962812A1, Japanese Patent Laid-open 349591/2000, 7683/2000 and 72711/2000.

The present invention is explained by the following examples but the invention is not limited to these examples.

EXAMPLES

Synthesis Example 1: Synthesis of Compound D-1
(1) Synthesis of 3-tribromomethanesulfonylbenzoic acid In 1000 ml of water were dissolved 181 g (1 mole) of 3-sulfinobenzoic acid, 80 g (2 moles) of sodium hydroxide, 233 g (2 moles) of sodium chloroacetate, and 5.1 g (0.05 mole) of sodium bromide, and after stirring the solution at 65° C. for 6 hours, the reaction mixture was cooled to room temperature. The thus obtained mixture is referred to as reaction mixture (1).

On the other hand, 294 g (7.35 moles) of sodium hydroxide was dissolved in 2000 ml of water and while keeping the solution at a temperature of 10° C. or lower, 180 ml (3.5 moles) of bromine was gradually added dropwise to the solution. To the thus obtained aqueous solution of NaOBr was gradually added dropwise the reaction mixture (1). In this case, care was taken so that the reaction temperature did not exceed 20° C. After stirring the mixture at 20° C. for one hour, the reaction mixture was poured to 4000 ml of an aqueous solution of 2 mol/L hydrochloric acid to precipitate crude crystals. The crude crystals were recovered by filtration, sufficiently washed with water, dried, and washed with 1000 ml of acetonitrile followed by drying to obtain 375 g of 3-tribromomethanesulfonylbenzoic acid (yield 86%, white crystals).

(2) Synthesis of 3-tribromomethanesulfonyl benzoylchloride

To 375 g (0.86 mole) of 3-tribromomethanesulfonyl benzoic acid were added 1 ml of dimethylformamide and 500 ml of thionyl chloride and the mixture was refluxed for one hour. The reaction mixture was filtered and 3000 ml of hexane was added to the filtrate to precipitate crystals. The crystals were recovered by filtration and dried to obtain 366 g of 3-tribromomethanesulfonyl benzoylchloride (yield 94%, white crystals).

(3) Synthesis of Compound D-1

A mixed solution of 0.96 g of n-butylamine and 20 ml of methanol was ice-cooled and 2.0 g of 3-tribromomethanesulfonyl benzoylchloride was added to the solution. After stirring the mixture at room temperature for 2 hours, 40 ml of an aqueous diluted hydrochloric acid solution was added to the reaction mixture to deposit white crystals. The crystals were recovered by filtration, sufficiently washed with water, and dried to obtain 1.90 g of Compound D-1 (yield 88%, white crystals, melting point 168° C.).

$^1$H NMR (300 MHz, DMSO): 8.86(t, J=5.4 Hz, 1H), 8.62(s, 1H), 8.36(d, J=7.5 Hz, 1H), 8.31(d, J=7.8 Hz, 1H), 7.87(t, J=7.8 Hz, 1H), 3.2–3.3(m, 2H), 1.48–1.58(m, 2H), 1.30–1.38(m, 2H), 0.91(t, J=7.2 Hz, 3H)

Synthesis Example 2: Synthesis of Compound D-2

A mixed solution of 0.96 g of iso-butylamine and 20 ml of methanol was ice-cooled and 2.0 g of 3-tribromomethanesulfonyl benzoylchloride was added to the solution. After stirring the mixture at room temperature for one hour, 40 ml of an aqueous diluted hydrochloric acid solution was added to the reaction mixture to deposit white crystals The crystals were recovered by filtration, sufficiently washed with water, and dried to obtain 1.95 g of Compound D-2 (yield 90%, white crystals, melting point 114° C.). $^1$H NMR (300 MHz, DMSO): 8.88(t, J=5.6 Hz, 1H), 8.62(s, 1H), 8.37(d, J=7.9 Hz, 1H), 8.31(d, J=7.0 Hz, 1H), 7.88(t, J=7.9 Hz, 1H), 3.12(t, J=6.5 Hz, 2H), 1.89(m, 1H), 0.94(d, J=6.7 Hz, 6H)

Synthesis Example 3: Synthesis of Compound D-3

A mixed solution of 1.15 g of n-amylamine and 20 ml of methanol was ice-cooled and 2.0 g of 3-tribromomethanesulfonyl benzoylchloride was added to the solution. After stirring the mixture at room temperature for 30 minutes, 40 ml of an aqueous diluted hydrochloric acid solution was added to the reaction mixture to deposit white crystals. The crystals were recovered by filtration, sufficiently washed with water, and dried to obtain 1.99 g of Compound D-3 (yield 90%, white crystals, melting point 144° C.).

$^1$H NMR (300 MHz, DMSO): 8.86(t, J=5.4 Hz, 1H), 8.62(s, 1H), 8.36(d, J=7.8 Hz, 1H), 8.31(d, J=7.2 Hz, 1H), 7.87(t, J=7.8 Hz, 1H), 3.2–3.3(m, 2H), 1.5–1.6(m, 2H), 1.2–1.4(m, 4H), 0.88(t, J=6.9 Hz, 3H)

Synthesis Example 4: Synthesis of Compound D-4

A mixed solution of 1.15 g of iso-amylamine and 20 ml of methanol was ice-cooled and 2.0 g of 3-tribromomethanesulfonyl benzoylchloride was added to the solution. After stirring the mixture at room temperature for 30 minutes, 40 ml of an aqueous diluted hydrochloric acid solution was added to the reaction mixture to deposit white crystals. The crystals were recovered by filtration, sufficiently washed with water, and dried to obtain 1.88 g of Compound D-4 (yield 85%, white crystals, melting point 179° C.).

$^1$H NMR (300 MHz, DMSO): 8.84(t, J=5.4 Hz, 1H), 8.62(s, 1H), 8.36(d, J=7.8 Hz, 1H), 8.31(d, J=7.2 Hz, 1H), 7.88(t, J=7.8 Hz, 1H), 3.1–3.2(m, 2H), 1.5–1.7(m, 1H), 1.44(q, J=6.9 Hz, 2H), 0.91(d, J=6.6 Hz, 6H)

Synthesis Example 5: Synthesis of Compound D-24

A mixed solution of 0.75 g of allylamine and 20 ml of methanol was ice-cooled and 2.0 g of 3-tribromomethanesulfonyl benzoylchloride was added to the solution. After stirring the mixture at room temperature For 30 minutes, 40 ml of an aqueous diluted hydrochloric acid solution was added to the reaction mixture to deposit white crystals The crystals were recovered by filtration, sufficiently washed with water, and dried to obtain 2.00 g of Compound D-24 (yield 96%, white crystals, melting point 156° C.).

Synthesis Example 6: Synthesis of Compound D-5

In a mixed solution of 40 ml of methylene chloride and 40 ml of water were dissolved 4.9 g (0.01 mole) of Compound D-1 and 3.8 g (0.03 mole) of sodium thiosulfate, and the solution obtained was stirred at room temperature for 2 hours. The reaction mixture was extracted with methylene chloride, the organic layer was washed twice with water, dried over magnesium sulfate, and recovered by filtration. The filtrate was concentrated to obtain 2.3 g of the white crystals of Compound D-5 (yield 56%).

The structures of the compounds synthesized by Synthesis Examples 1 to 6 are shown below.

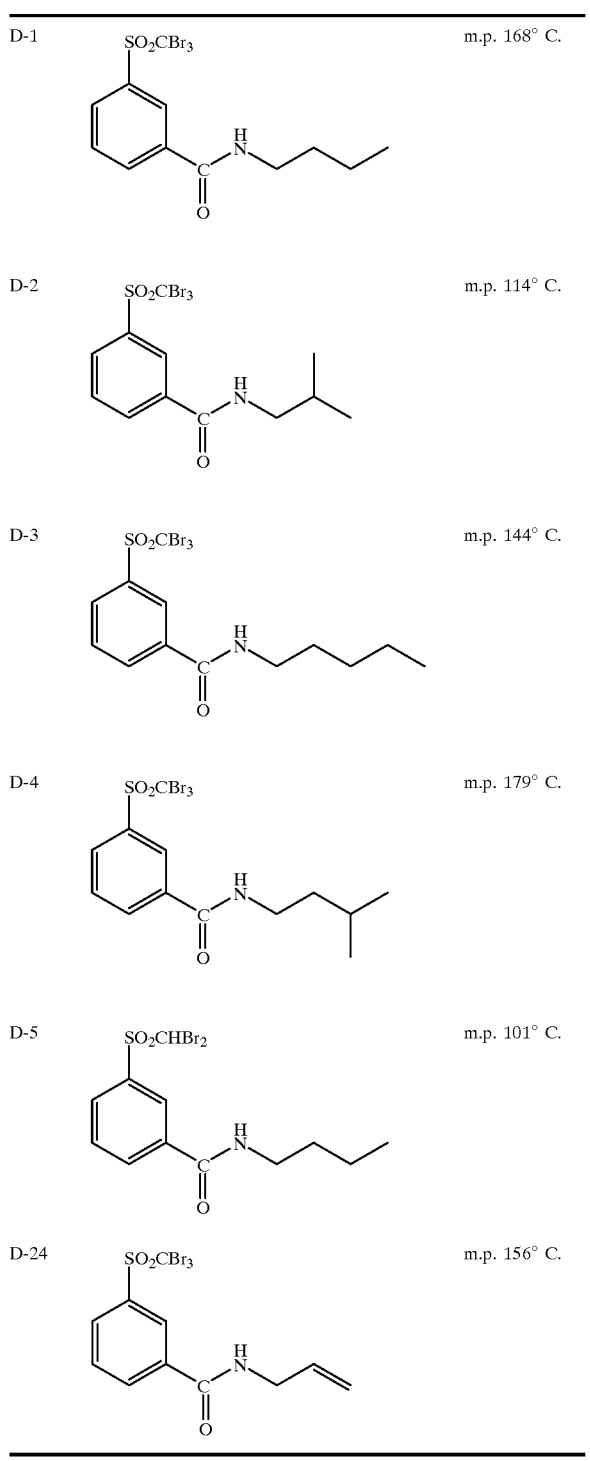
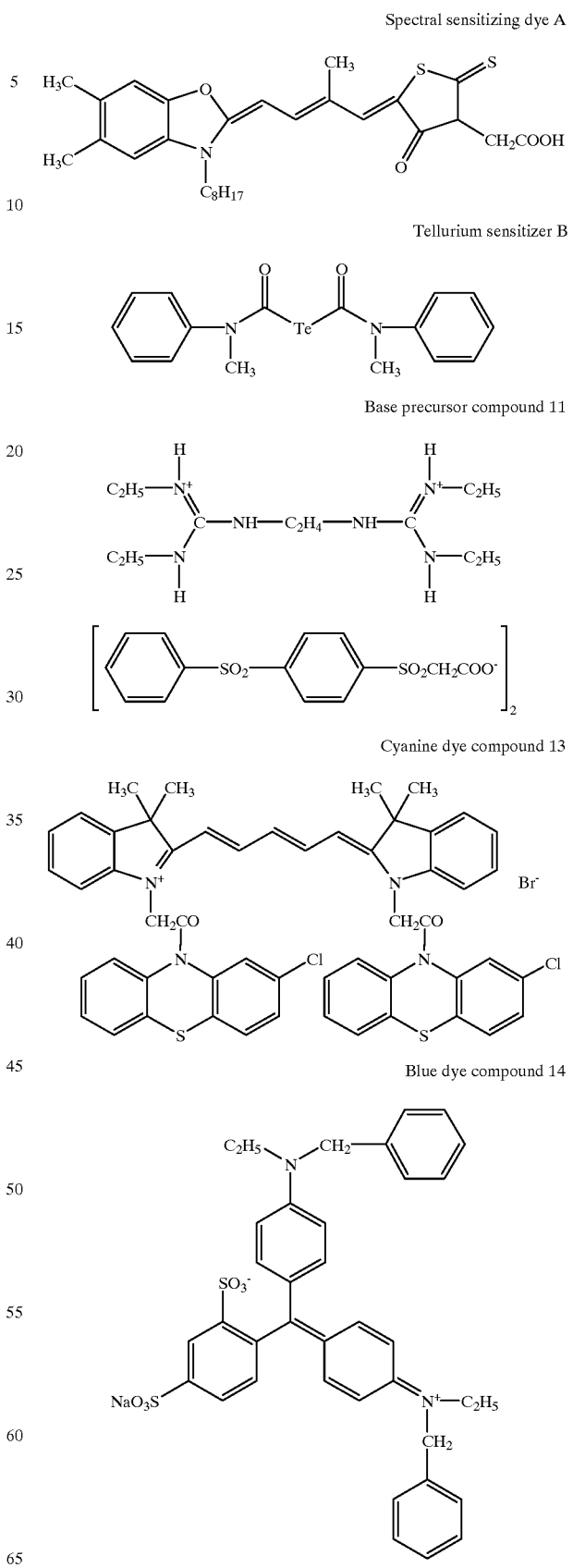
Thermally processed image recording materials were prepared using the polyhalogenomethylsulfonyl compounds of the invention and the photographic performances were evaluated. The results are shown in following Use Examples 1 and 2.
Use Example 1
The structures of the compounds used in Use Example are shown below.

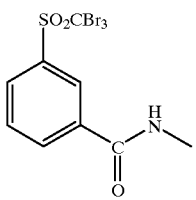
P-1

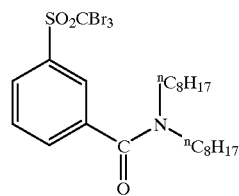
P-2

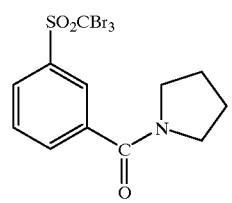
P-3

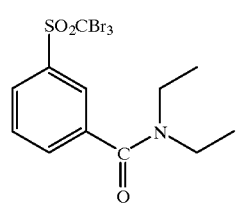
P-4

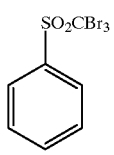
P-5

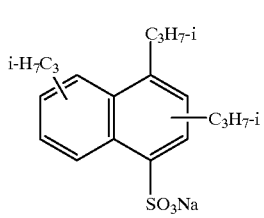
Compound C

1. Preparation of PET Support

Using terephthalic acid and ethylene glycol, PET having an intrinsic viscosity IV of 0.66 (measured in phenol/tetrachlqroethane=6/4 (weight ratio) at 25° C.) was obtained in a conventional manner. The PET was pelletized, and the pellets were dried at 130° C. for 4 hours, melted at 300° C., extruded from a T-die, and quenched to prepare an unstretched film having such a thickness that the film thickness after thermal fixation should become 175 μm.

The film was stretched along the longitudinal direction by 3.3 times using rollers having different peripheral speeds and then stretched along the transverse direction by 4.5 times using a tenter. In this case, the temperatures were 110° C. and 130° C., respectively. Thereafter, the film was subjected to thermal fixation at 240° C. for 20 seconds and relaxed by 4% along the transverse direction at the same temperature. Then, after chucks of the tenter were released, the both edges of the film were knurled, and the film was rolled up at 4 kg/cm$^2$ to provide a roll of the film having a thickness of 175 μm.

2. Surface Corona Discharging Treatment

Using a solid state corona discharging treatment machine Model 6KVA manufactured by Piller Inc., both surfaces of the support were treated at room temperature at 20 m/minute. In this case, from the read out values of the electric current and the voltage, it was seen that the treatment of 0.375 kV•A•minute/m$^2$ was applied to the support. The treated frequency in this case was 9.6 kHz and the gap clearance between the electrode and the dielectric roll was 1.6 mm.

3. Preparation of Undercoated Support (1) Preparation of Coating Solution for Undercoat Layer Coating solutions of the following formulations (1) to (3) were prepared.

| Formulation (1) (for undercoat layer on photosensitive layer side) | |
|---|---|
| Pesresin A-515GB made by Takamatsu Yushi K.K. (30% by weight solution) | 234 g |
| Polyethylene glycol monononylphenyl ether (mean ethylene oxide number = 8.5, 10% by weight solution) | 21.5 g |
| MP-1000 made by Soken Kagaku K.K. (polymer microparticles, mean particle size: 0.4 μm) | 0.91 g |
| Distilled water | 744 ml |
| Formulation (2) (for 1st layer on back surface) | |
| Butadiene-styrene copolymer latex (solid content: 40% by weight, weight ratio of butadiene/styrene = 32/68) | 158 g |
| 2,4-Dichloro-6-hydroxy-S-triazine sodium salt (8% by weight aqueous solution) | 20 g |
| 1% by weight Aqueous solution of sodium laurylbenzenesulfonate | 10 ml |
| Distilled water | 854 ml |
| Formulation (3) (for 2nd layer on back surface side) | |
| SnO$_2$/SbO (weight ratio: 9/1, mean particle size: 0.038 μm, 17% by weight dispersion) | 84 g |
| Gelatin (10% aqueous solution) | 89.2 g |
| Metorose TC-5 made by Shin-Etsu Chemical Co., Ltd. (2% aqueous solution) | 8.6 g |
| MP-1000 (polymer microparticles) made by Soken Kagaku K.K. | 0.01 g |
| 1% by weight Aqueous solution of sodium dodecylbenzenesulfonate | 10 ml |
| NaOH (1%) | 6 ml |
| Proxel (made by ICI Co.) | 1 ml |
| Distilled water | 805 ml |

(2) Preparation of Undercoated Support

After applying the aforementioned corona discharging treatment to both surfaces of the aforementioned biaxially stretched polyethylene terephthalate support having a thickness of 175 μm, one surface (photosensitive layer coating surface side) thereof was coated with the undercoating solution of Formulation (1) by a wire bar in a wet coating amount of 6.6 ml/m$^2$ (per one surface) and dried at 180° C. for 5 minutes. Then, the back surface thereof was coated with the undercoating solution of Formulation (2) by a wire bar in a wet coating amount of 5.7 ml/m$^2$ and dried at 180° C. for 5 minutes. Further, the back surface thus coated was coated with the undercoating solution of Formulation (3) by a wire bar in a wet coating amount of 7.7 ml/m$^2$ and dried at 180° C. for 6 minutes to prepare an undercoated support.

4. Preparation of Coating Solution for Back Surface (1) Preparation of Solid Microparticle Dispersion (a) of Base Precursor 64 g of Base precursor compound 11, 28 g of diphenylsulfone and 10 g of a surface active agent, Demor N (manufactured by Kao Corporation), were mixed with 220 ml of distilled water, and the mixture was beads-dispersed using a sand mill (¼ Gallon Sand Grinder Mill, manufactured by Imex Co.) to obtain Solid microparticle dispersion (a) of the base precursor compound having a mean particle size of 0.2 μm.

(2) Preparation of Dye Solid Microparticle Dispersion 9.6 g of Cyanine dye compound 13 and 5.8 g of sodium p-dodecylbenzenesulfonate were mixed with 305 ml of distilled water and the mixture was beads-dispersed using a sand mill (¼ Gallon Sand Grinder Mill, manufactured by Imex Co.) to obtain a dye solid microparticle dispersion having a mean particle size of 0.2 μm.

(3) Preparation of Coating Solution for Antihalation Layer 17 g of gelatin, 9.6 g of polyacrylamide, 70 g of the aforementioned Solid microparticle dispersion (a) of the base precursor, 56 g of the aforementioned dye solid microparticle dispersion, 1.5 g of polymethyl methacrylate microparticles (mean particle size 6.5 μm), 0.03 g of benzoisothiazolinone, 2.2 g of sodium polyethylenesulfonate, 0.2 g of Blue dye compound 14 and 844 ml of water were mixed to prepare a coating solution for antihalation layer.

5. Preparation of Coating Solution for Back Surface Protective Layer

In a container kept at 40° C., 50 g of gelatin, 0.2 g of sodium polystyrenesulfonate, 2.4 g of N,N-ethylenebis (vinylsulfonacetamide), 1 g of sodium t-octylphenoxyethoxyethanesulfonate, 30 mg of benzoisothiazolinone, 37 mg of N-perfluorooctylsulfonyl-N-propylalanine potassium salt, 0.15 g of polyethyleneglycol mono(N-perfluorooctylsulfonyl-N-propyl-2-aminoethyl) ether [average polymerization degree of ethylene oxide: 15], 32 mg of $C_8F_{17}SO_3K$, 64 mg of $C_8F_{17}SO_2N(C_3H_7)(CH_2CH_2O)_4(CH_2)_4$—$SO_3Na$, 8.8 g of an acrylic acid/ethyl acrylate copolymer (copolymerization ratio (by weight): 5/95), 0.6 g of Aerosol OT (manufactured by American Cyanamid Company), 1.8 g (as liquid paraffin) of a liquid paraffin emulsion and 950 ml of water were mixed to form a coating solution for a back surface protective layer.

6. Preparation of Silver Halide Emulsion 1

1421 ml of distilled water was added with 8.0 ml of a 1% by weight potassium bromide solution, and further added with 8.2 ml of 1 mol/L nitric acid and 20 g of phthalized gelatin. Separately, Solution A was prepared by adding distilled water to 37.04 g of silver nitrate to dilute it to 159 ml, and Solution B was prepared by diluting 32.6 g of potassium bromide with distilled water to a volume of 200 ml. To the aforementioned mixture maintained at 37° C. and stirred in a titanium-coated stainless steel reaction vessel, the whole volume of Solution A was added by the control double jet method over 1 minute at a constant flow rate while pAg was maintained at 8.1. Solution B was also added by the control double jet method. Then, the mixture was added with 30 ml of 3.5% by weight aqueous hydrogen peroxide solution, and further added with 36 ml of a 3% by weight aqueous solution of benzimidazole. Separately, Solution A2 was prepared by diluting Solution A with distilled water to a volume of 317.5 ml, and Solution B2 was prepared by dissolving tripotassium hexachloroiridate in Solution B in such an amount that its final concentration should become $1×10^{-4}$ mole per mole of silver, and diluting the obtained solution with distilled water to a volume twice as much as the volume of Solution B, 400 ml. The whole volume of Solution A2 was added to the mixture again by the control double jet method over 10 minutes at a constant flow rate while pAg was maintained at 8.1. Solution B2 was also added by the control double jet method. Then, the mixture was added with 50 ml of a 0.5% by weight solution of 2-mercapto-5-methylbenzimidazole in methanol. After pAg was raised to 7.5 with silver nitrate, the mixture was adjusted to pH 3.8 using 0.5 mol/L sulfuric acid, and the stirring was stopped. Then, the mixture was subjected to precipitation, desalting and washing with water, added with 3.5 g of deionized gelatin and 1 mol/L sodium hydroxide to be adjusted to pH 6.0 and pAg of 8.2 to form a silver halide dispersion.

The grains in the completed silver halide emulsion were pure silver bromide grains having a mean spherical diameter of 0.053 μm and a variation coefficient of 18% in terms of spherical diameter. The grain size and others were obtained from averages for 1000 grains by using an electron microscope. The [100] face ratio of these grains were determined to be 85% by the Kubelka-Munk method.

The aforementioned dispersion was added with 0.035 g of benzoisothiazolinone (added as a 3.5% by weight methanol solution of the compound) with stirring at 38° C., after 40 minutes since then, added with the solid dispersion (an aqueous gelatin solution) of Spectral sensitizing dye A described above in an amount of $5×10^{-3}$ mole per mole of silver. After 1 minutes, the mixture was warmed to 47° C., and after 20 minutes, added with $3×10^{-5}$ mole of sodium benzenethiosulfonate per mole of silver. Further after 2 minutes, the mixture was added with Tellurium sensitizer B in an amount of $5×10^{-5}$ mole per mole of silver followed by ripening for 90 minutes. Immediately before finishing the ripening, the mixture was added with 5 ml of a 3.5% by weight methanol solution of N,N'-dihydroxy-N"-diethylmelamine, and after lowering the temperature to 31° C., added with 5 ml of a 3.5% by weight methanol solution of phenoxyethanol, $7×10^{-3}$ mole of 5-methyl-2-mercaptobenzimidazole per mole of silver, and $6.4×10^{-3}$ mole of 1-phenyl-2-heptyl-5-mercapto-1,3,4-triazole per mole of silver to prepare Silver halide emulsion 1.

7. Preparation of Silver Halide Emulsion 2

In the same manner as the preparation of Silver halide emulsion 1 except that the liquid temperature upon forming the grains was changed from 37° C. to 50° C., a pure silver bromide cubic grain dispersion having a mean grain size of 0.08 μm as spheres and a variation coefficient of 15% for size as spheres was prepared. Further, as in the case of Silver halide emulsion 1, the steps of precipitation, desalting, washing with water and dispersion were performed. Furthermore, in the same manner as in the case of Silver halide emulsion 1 except that the addition amount of Spectral sensitizing dye A was changed to $4.5×10^{-3}$ mole per mole of silver, the spectral sensitizer, the chemical sensitizer, 5-methyl-2-mercaptobenzimidazole and 1-phenyl-2-heptyl-5-mercapto-1,3,4-traizole were added to the dispersion to obtain Silver halide emulsion 2.

8. Preparation of Silver Halide Emulsion 3

In the same manner as the preparation of Silver halide emulsion 1 except that the liquid temperature upon forming the grains was changed from 37° C. to 27° C., a pure silver bromide cubic grain dispersion having a mean grain size of 0.038 μm as spheres and a variation coefficient of 20% for size as spheres was prepared. Further, as in the case of Silver halide emulsion 1, the steps of precipitation, desalting, washing with water and dispersion were performed. Furthermore, in the same manner as in the case of Silver halide emulsion 1 except that the addition amount of Spectral sensitizing dye A was changed to $6 \times 10^{-3}$ mole per mole of silver, the spectral sensitizer, the chemical sensitizer, 5-methyl-2-mercaptobenzimidazole and 1-phenyl-2-heptyl-5-mercapto-1,3,4-traizole were added to the dispersion to obtain Silver halide emulsion 2.

9. Preparation of Mixed Emulsion A for Coating Solution

70% by weight Silver halide emulsion 1, 15% by weight Silver halide emulsion 2 and 15% by weight Silver halide emulsion 3 were mixed, and added with benzothiazolium iodide in an amount of $7 \times 10^{-3}$ mole per mole of silver as a 1% by weight aqueous solution.

10. Preparation of Scaly Fatty Acid Silver Salt 87.6 kg of behenic acid (Edenor C22-85R, trade name, manufactured by Henkel Co.), 423 L of distilled water, 49.2 L of a 5 mol/L aqueous solution of NaOH, and 120 L of tert-butanol were mixed and allowed to react with stirring at 75° C. for one hour to obtain a solution of sodium behenate. Separately, 206.2 L of an aqueous solution containing 40.4 kg of silver nitrate (pH 4.0) was prepared and kept at 10° C. A mixture of 635 L of distilled water and 30 L of tert-butanol contained in a reaction vessel kept at 30° C. was added with the whole amount of the aforementioned sodium behenate solution and the whole amount of the aqueous silver nitrate solution at constant flow rates over the periods of 62 minutes and 10 seconds, and 60 minutes, respectively. In this case, they were added in such a manner that only the aqueous silver nitrate solution was added for 7 minutes and 20 seconds after starting the addition of the aqueous silver nitrate solution, and for 9 minutes and 30 seconds after finishing the addition of the aqueous silver nitrate solution, only the sodium behenate solution was added. In this operation, the outside temperature was controlled so that the temperature in the reaction vessel should be 30° C. and the liquid temperature should be constant. The piping of the addition system for the sodium behenate solution was warmed by steam trace and the steam opening was controlled such that the liquid temperature at the outlet orifice of the addition nozzle should be 75° C. The piping of the addition system for the aqueous silver nitrate solution was maintained by circulating cold water outside a double pipe. The addition position of the sodium behenate solution and the addition position of the aqueous silver nitrate solution were arranged symmetrically with respect to the stirring axis as the center, and the positions are controlled at heights for not contacting with the reaction mixture.

After finishing the addition of the sodium behenate solution, the mixture was left with stirring for 20 minutes at the same temperature and then the temperature was decreased to 25° C. Thereafter, the solid content was recovered by a suction filtration and the solid content was washed with water until electric conductivity of the filtrate became 30 $\mu$S/cm. Thus, a fatty acid silver salt was obtained. The solid content was stored as a wet cake without being dried.

When the shape of the obtained silver behenate grains was evaluated by an electron microscopic photography, the grains were scaly crystals having a=0.14 $\mu$m, b=0.4 $\mu$m, and c=0.6 $\mu$m in mean values, a mean aspect ratio of 5.2, a mean diameter as spheres of 0.52 $\mu$m, and a variation coefficient of 15% for mean diameter as spheres (the shape of the silver behenate grains was approximated to be a rectangular parallelepiped, and the sides of the rectangular parallelepiped were defined to be a, b and c from the shortest side.).

To the wet cake corresponding to 100 g of the dry solid content was added with 7.4 g of polyvinyl alcohol (PVA-217, trade name) and water to make the total amount 385 g, and the mixture was pre-dispersed by a homomixer.

Then, the pre-dispersed stock dispersion was treated three times by using a dispersing machine (Microfluidizer-M-110S-EH; trade name, manufactured by Microfluidex International Corporation, using G10Z interaction chamber) with a pressure controlled to be 1750 kg/cm$^2$ to obtain a silver behenate dispersion. During the cooling operation, a dispersion temperature of 18° C. was achieved by providing coiled heat exchangers fixed before and after the interaction chamber and controlling the temperature of the refrigerant.

11. Preparation of 25% by Weight Dispersion of Reducing Agent 10 kg of 1,1-bis(2-hydroxy-3,5-dimethylphenyl)-3,5,5-trimethylhexane and 10 kg of a 20% by weight aqueous solution of denatured polyvinyl alcohol (Poval MP203, manufactured by KURARAY Co., LTD.) were added with 16 kg of water, and mixed sufficiently to form a slurry. The slurry was fed by a diaphragm pump to a sand mill of horizontal type (UVM-2, manufactured by Imex Co.) containing zirconia beads having a mean diameter of 0.5 mm, and dispersed for 3 hours and 30 minutes. Then, the slurry was added with 0.2 g of benzothiazolinone sodium salt and water so that the concentration of the reducing agent should become 25% by weight to obtain a reducing agent dispersion. The reducing agent particles contained in the reducing agent dispersion obtained as described above had a median diameter of 0.42 $\mu$m and the maximum particle size of 2.0 $\mu$m or shorter. The reducing agent dispersion was filtered through a polypropylene filter having a pore size of 10.0 $\mu$m to remove dusts and so forth, and stored.

12. Preparation of 10% by Weight Dispersion of Mercapto Compound 5 kg of 1-phenyl-2-heptyl-5-mercapto-1,3,4-triazole and 5 kg of a 20% by weight aqueous solution of denatured polyvinyl alcohol (Poval MP203, manufactured by KURARAY CO., LTD.) were added with 8.3 kg of water and mixed sufficiently to form a slurry. The slurry was fed by a diaphragm pump to a sand mill of horizontal type (UVM-2, manufactured by Imex Co.) containing zirconia beads having a mean diameter of 0.5 mm, and dispersed for 6 hours. Then, the slurry was added with water so that the concentration of the mercapto compound should become 10% by weight to obtain a mercapto compound dispersion. The mercapto compound particles contained in the mercapto compound dispersion obtained as described above had a median diameter of 0.40 $\mu$m and the maximum particle size of 2.0 $\mu$m or shorter. The mercapto compound dispersion was filtered through a polypropylene filter having a pore size of 10.0 $\mu$m to remove dusts and so forth, and stored. The dispersion was filtered through a polypropylene filter having a pore size of 10 $\mu$m immediately before use.

13. Preparation of Solid Microparticle Dispersion of Compound of Formula (1) According to the Present Invention 30 g of each of the compounds of the formula (1) shown in Table 1 was added with 4 g of MP polymer (MP-203 manufactured by KURARAY CO., LTD.), 0.25 g of Compound C and 66 g of water and the mixture was stirred sufficiently to form a slurry. Thereafter, 200 g of zirconia silicate beads having a diameter of 0.5 mm were placed in a vessel together with the slurry and the slurry was dispersed by a dispersing machine (1/16 G Sand Grinder Mill; manufactured by Imex Co.) for 5 hours to prepare a solid microparticle dispersion. In the particles, 80% by weight of the particles had a diameter of 0.3 $\mu$m to 1.0 $\mu$m. Each of Comparative Compounds P-1 to P-5 was also dispersed in the same manner as above.

14. Preparation of 10% by Weight Dispersion of Phthalazine Compound

A solution of 10 g of 6-isopropylphthalazine dissolved in 90 g of methanol was used.

15. Preparation of 20% by Weight Dispersion of Pigment 64 g of C.I. Pigment Blue 60 and 6.4 g of Demor N manufactured by Kao Corporation were added with 250 g of water and mixed sufficiently to provide a slurry. Then, 800 g of zirconia beads having a mean diameter of 0.5 mm were placed in a vessel together with the slurry and the slurry was dispersed by a dispersing machine (¼ G Sand Grinder Mill; manufactured by Imex Co.) for 25 hours to obtain a pigment dispersion. The pigment particles contained in the pigment dispersion obtained as described above had a mean particle size of 0.21 $\mu$m.

16. Preparation of 40% by Weight SBR Latex

An SBR latex purified by ultrafiltration (UF) was obtained as follows.

The SBR latex mentioned below diluted by 10 times with distilled water was diluted and purified by using an UF-purification module FS03-FC-FUY03A1 (manufactured by Daisen Membrane System K.K.) until the ion conductivity became 1.5 mS /cm, and added with Sandet-BL (manufactured by SANYO CHEMICAL INDUSTRIES, LTD.) to a concentration of 0.22% by weight. Further, the latex was added with NaOH and $NH_4OH$ so that the ratio $Na^+$ ion:$NH_4^+$ ion should become 1:2.3 (molar ratio) to adjust pH to 8.4. At this point, the concentration of the latex was 40% by weight.

[SBR latex: a latex of -St(68)-Bu(29)-AA(3), wherein the numerals in the parentheses indicate the contents in terms of % by weight, St represents styrene, Bu represents butadiene and AA represents acrylic acid]

The latex had the following characteristics: mean particle size of 0.1 $\mu$m, concentration of 45%, equilibrated moisture content at 25° C., relative humidity 60% of 0.6% by weight, ion conductivity of 4.2 mS/cm (measured for the latex stock solution (40%) by using a conductometer, CM-30S, manufactured by Toa Electronics, Ltd., at 25° C.), and pH of 8.2.

17. Preparation of Coating Solution for Emulsion Layer (Photosensitive Layer)

1.1 g of the 20% by weight aqueous dispersion of the pigment obtained above, 103 g of the organic acid silver salt dispersion, 2 g of the 20% by weight aqueous solution of polyvinyl alcohol, PVA-205 (manufactured by KURARAY CO. LTD.), 25 g of the 25% by weight dispersion of the reducing agent, a compound of the formula (1) (type and amount thereof are shown in Table 1), 6.2 g of the 10% dispersion of the mercapto compound, 130 g of the 40% by weight SBR latex purified by ultrafiltration (UF) and undergone pH adjustment, and 16 ml of the 10% by weight methanol solution of the phthalzine compound were mixed and added to 10 g of the aforementioned Silver halide emulsion A, and mixed sufficiently to prepare a coating solution for an emulsion layer. The coating solution was fed to a coating die in such a feeding amount giving a coating amount of 70 ml/m² and coated.

The viscosity of the coating solution for emulsion layer described above was measured by a B-type viscometer manufactured by Tokyo Keiki K.K. and found to be 85 [mpa·s] at 40° C. (Rotor No. 1, 60 rpm).

The viscosity of the coating solution was measured at 25° C. by an RFS fluid spectrometer produced by Rheometric Far East Co., Ltd., and found to be 1500, 220, 70, 40 and 20 [mpa·s] at shear rates of 0.1, 1, 10, 100 and 1000 [1/second], respectively.

18. Preparation of Coating Solution for Intermediate Layer on the Emulsion Layer Surface 772 g of an aqueous solution of 10% by weight polyvinyl alcohol, PVA-205 (manufactured by KURARAY CO., LTD.), 5.3 g of the 20% by weight dispersion of the pigment, and 226 g of a 27.5% by weight latex of methyl methacrylate/styrene/butyl acrylate/hydroxyethyl methacrylate/acrylic acid copolymer (copolymerization ratio (by weight): 64/9/20/5/2) were added with 2 ml of a 5% by weight aqueous solution of Aerosol OT (manufactured by American Cyanamid Company), 10.5 ml of a 20% by weight aqueous solution of phthalic acid diammonium salt and water in such an amount giving a total amount of 880 g to form a coating solution for intermediate layer. This coating solution was fed to a coating die in such an amount that gave a coating-amount of 10 ml/m².

The viscosity of the coating solution measured by a B-type viscometer at 40° C. (Rotor No. 1, 60 rpm) was 21 [mPa·s].

19. Preparation of Coating Solution for 1st Protective Layer on Emulsion Layer Surface 64 g of inert gelatin was dissolved in water, added with 80 g of a 27.5% by weight latex solution of methyl methacrylate/styrene/butyl acrylate/hydroxyethyl methacrylate/acrylic acid copolymer (copolymerization ratio (by weight): 64/9/20/5/2), 64 ml of a 10% by weight methanol solution of phthalic acid, 74 ml of a 10% by weight aqueous solution of 4-methylphthalic acid, 28 ml of 0.5 mol/L sulfuric acid, 5 ml of a 5% by weight aqueous solution of Aerosol OT (manufactured by American Cyanamid Company), 0.5 g of phenoxyethanol, 0.1 g of benzoisothiazolinone, and water in such an amount that gave a total amount of 750 g to form a coating solution. The coating solution was mixed with 26 ml of 4% by weight chromium alum by a static mixer immediately before coating, and fed to a coating die in such an amount that gave a coating amount of 18.6 ml/m².

The viscosity of the coating solution measured by a B-type viscometer (Rotor No. 1, 60 rpm) at 40° C. was 17 [mPa·s].

20. Preparation of Coating Solution for 2nd Protective Layer on Emulsion Layer Surface 80 g of inert gelatin was dissolved in water, added with 102 g of a 27.5% by weight latex solution of methyl methacrylate/styrene/butyl acrylate/hydroxyethyl methacrylate/acrylic acid copolymer (copolymerization ratio (by weight): 64/9/20/5/2), 3.2 ml of a 5% by weight solution of N-perfluorooctylsulfonyl-N-propylalanine potassium salt, 32 ml of a 2% by weight aqueous solution of polyethylene glycol mono(N-perfluorooctylsulfonyl-N-propyl-2-aminoethyl) ether [average polymerization degree of ethylene oxide=15], 23 ml of a 5% by weight aqueous solution of Aerosol OT (manufactured by American Cyanamid Company), 4 g of polymethyl methacrylate microparticles (mean particle size: 0.7 $\mu$m), 21 g of polymethyl methacrylate microparticles (mean particle size: 6.4 $\mu$m), 1.6 g of 4-methylphthalic acid, 8.1 g of phthalic acid, 44 ml of 0.5 mol/L sulfuric acid, 10 mg of benzoisothiazolinone and water in such an amount that gave a total amount of 650 g to provide a coating solution. The coating solution was mixed with 445 ml of a solution containing 4% by weight chromium alum and 0.67% by weight of phthalic acid by a static mixer immediately before coating to form a coating solution for surface protective layer, which was fed to a coating die in such an amount that gave a coating amount of 8.3 ml/m².

The viscosity of the coating solution measured by a B-type viscometer (Rotor No. 1, 60 rpm) at 40° C. was 9 [mPa·s].

21. Preparation of Thermally Processed Image Recording Material

On the back side of the aforementioned support having an undercoat layer, the coating solution for antihalation layer and the coating solution for back surface protective layer were simultaneously applied as stacked layers so that the applied solid content amount of the solid microparticle dye in the antihalation layer should be 0.04 g/m$^2$, and the applied amount of gelatin in the protective layer should be 1.7 g/m$^2$, and dried to form an antihalation back layer.

Then, on the side opposite to the back side, an emulsion layer (coated silver amount of the silver halide was 0.14 q/m$^2$), intermediate layer, first protective layer, and second protective layer were simultaneously applied in this order from the undercoat layer by the slide bead application method as stacked layers to form a sample of thermally processed image recording material.

The coating was performed at a speed of 160 m/min. The gap between the tip of coating die and the support was set to be 0.14 to 0.28 mm, and the coated width was controlled so that it spread by each 0.5 mm at both sides compared with the projecting slit width of the coating solution. The pressure in the reduced pressure chamber was adjusted to be lower than the atmospheric pressure by 392 Pa. In this case, handling, temperature and humidity were controlled so that the support should not be electrostatically charged and further electrostatic charge was eliminated by ionized wind immediately before the coating. In the subsequent chilling zone, the material was blown with air showing a dry-bulb temperature of 18° C. and a wet-bulb temperature of 12° C. for 30 seconds to cool the coating solutions. Then, in the floating type drying zone in a coiled shape, the material was blown with drying air showing a dry-bulb temperature of 30° C. and a wet-bulb temperature of 18° C. for 200 seconds.

Subsequently, the material was passed through a drying zone of 70° C. for 20 seconds, and then another drying zone of 90° C. for 10 seconds, and cooled to 25° C. to evaporate the solvent in the coating solution. The average wind velocities of the wind applied to the coated layer surface in the chilling zone and the drying zones were 7 m/sec.

22. Evaluation of Photographic Performance

After each thermally processed image recording material was light-exposed by a laser sensitometer (details are given below), the thermally processed image recording material was treated at 118° C. for 5 seconds and then treated at 122° C. for 16 seconds (heat development).

Laser sensitometer:

Combination of two diode lasers of 660 nm showing an output of 35 mw.

Single mode.

Gaussian beam spot 1/e$^2$ of 100 μm.

The light source was proceeded along the sub-scanning direction at a pitch of 25 μm and each pixel was written 4 times.

The evaluation of the image obtained was performed by using a Macbeth TD904 densitometer (visible density). The measurement results were evaluated as Dmin, sensitivity (evaluated by a relative value of a reciprocal of a ratio of exposure amounts giving a density higher than Dmin by 1.0, and the sensitivity of the thermally processed image recording material of Experiment No. 1 shown in Table 1 below was defined as 100), Dmax, and gradation (contrast) (fresh photographic properties). The contrast was expressed by a gradient of a straight line connecting the points at the densities from which the value for Dmin was subtracted, 0.5 and 1.5, with the abscissa being a logarithm of the exposure amount.

As for the evaluation of image storage stability, Image storage stability 1 shows the change of the photographic properties after storing the thermally processed image recording materials after heat development in the dark for 24 hours at a temperature of 60° C. and relative humidity of 50%, and Image storage stability 2 shows the change of the photographic properties after storing them for 24 hours under the light irradiation of 10,000 luces at a temperature of 40° C. and relative humidity of 50%.

TABLE 1

| No. | Compound of formula (1) | Added amount (mol/mol-Ag) | Fresh photographic property | | | | Image storage stability-1 (stored in dark, 60° C., 50%) | | Image storage stability-2 (stored in light, 40° C., 50%) | | Note |
| --- | --- | --- | --- | --- | --- | --- | --- | --- | --- | --- | --- |
| | | | Dmin | Sensitivity | Gradation | Dmax | Dmin | Dmax | Dmin | Dmax | |
| 1 | D-1 | 0.16 | 0.16 | 100 | 2.7 | 3.2 | 0.19 | 3.1 | 0.18 | 3.2 | Example |
| 2 | D-2 | 0.16 | 0.16 | 98 | 2.7 | 3.1 | 0.19 | 3.1 | 0.18 | 3.1 | Example |
| 3 | D-3 | 0.16 | 0.16 | 102 | 2.7 | 3.2 | 0.18 | 3.2 | 0.18 | 3.1 | Example |
| 4 | D-4 | 0.16 | 0.16 | 99 | 2.7 | 3.2 | 0.19 | 3.2 | 0.18 | 3.2 | Example |
| 5 | D-14 | 0.16 | 0.16 | 99 | 2.7 | 3.1 | 0.21 | 3.1 | 0.20 | 3.1 | Example |
| 6 | P-1 | 0.16 | 0.16 | 100 | 2.7 | 3.0 | 0.35 | 3.0 | 0.28 | 2.9 | Comparative Example |
| 7 | P-2 | 0.16 | 0.16 | 99 | 2.7 | 3.2 | 0.56 | 2.8 | 0.42 | 3.0 | Comparative Example |
| 8 | P-3 | 0.16 | 0.16 | 102 | 2.7 | 3.1 | 0.45 | 2.9 | 0.39 | 3.0 | Comparative Example |
| 9 | P-4 | 0.16 | 0.19 | 104 | 2.6 | 3.2 | 0.39 | 3.0 | 0.35 | 3.1 | Comparative Example |
| 10 | P-5 | 0.16 | 0.17 | 99 | 2.7 | 3.2 | 0.42 | 3.0 | 0.37 | 3.1 | Comparative Example |

As seen from the results shown in Table 1, when the compounds of the invention were used for the thermally processed image recording materials, good photographic performance and good image storage stability could be obtained.

Use Example 2

The structures of the compounds used in Use Example 2 are shown below.

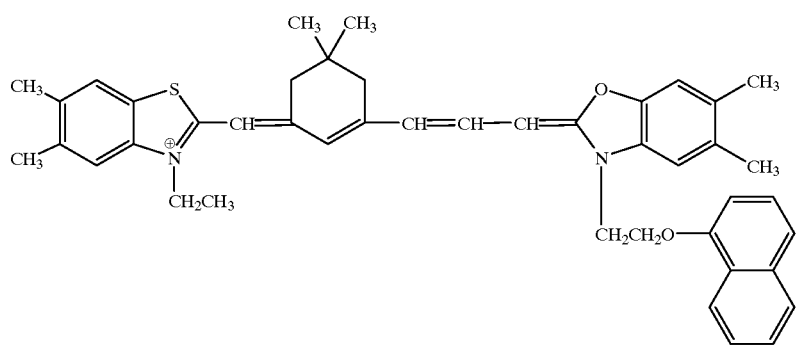
Sensitizing dye A
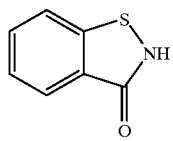
Compound A
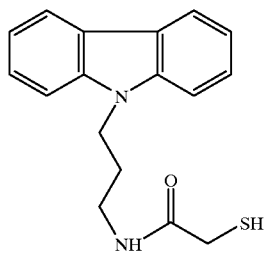
Compound B
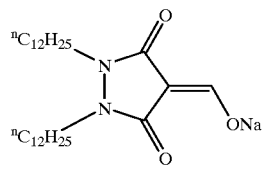
Ultrahigh contrast agent B
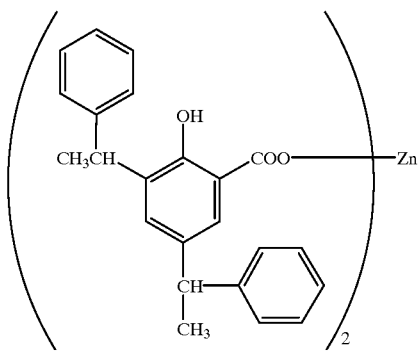
Compound Z
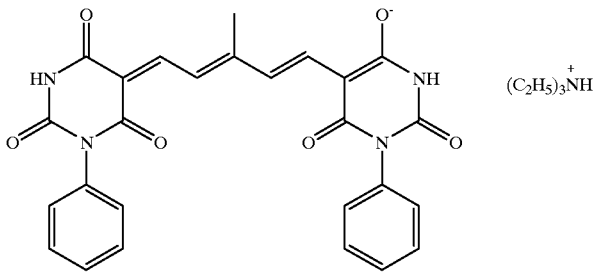
Dye A -continued

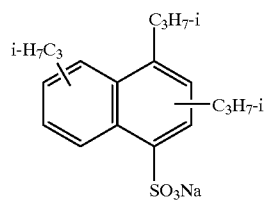
Compound C

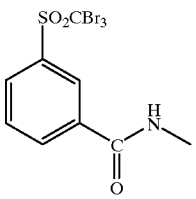
P-1

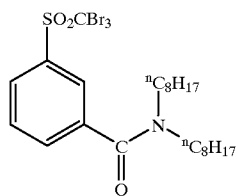
P-2

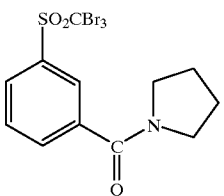
P-3

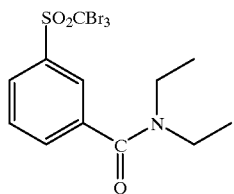
P-4

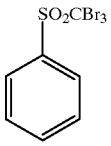
P-5

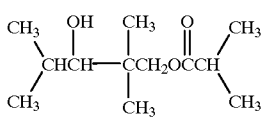

Compound D

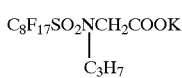

Compound E

CH₃—[benzene]—COOH, COOH

Compound F

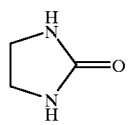

Compound S

1. Preparation of Silver Halide Emulsion (Emulsion A)

11 g of alkali-treated gelatin (calcium content of 2700 ppm or less), 30 mg of potassium bromide and 10 mg of sodium benzenesulfonate were dissolved in 700 ml of water, and the pH of the mixture was adjusted to pH 5.0 at a temperature of 40° C., and added with 159 ml of an aqueous solution containing 18.6 g of silver nitrate and an aqueous solution containing 1 mole/liter of potassium bromide, $5 \times 10^{-6}$ mole/liter of $(NH_4)_2RhCl_5$ $(H_2O)$, and $2 \times 10^{-5}$ mole/liter of $K_3IrCl_6$ by the control double jet method over a period of 6 minutes and 30 seconds, while the pAg was kept at 7.7. Then, the solution was added with 476 ml of an aqueous solution containing 55.5 g of silver nitrate and an aqueous halide salt solution containing 1 mole/liter of potassium bromide and $2 \times 10^{-5}$ mole/liter of $K_3IrCl_6$ by the control double jet method over a period of 28 minutes and 30 seconds, while the pAg was kept at 7.7. Thereafter, by lowering the pH to cause aggregation and precipitation to attain a desalting treatment. The mixture was added with 0.17 g of Compound A and 51.1 g of low molecular weight gelatin having an average molecular weight of 15,000 (calcium content: 20 ppm or less), and the pH and pAg of the mixture were adjusted to 5.9 and 8.0, respectively. The obtained grains were cubic grains having a mean grain size of 0.08 μm, a variation coefficient of 9% for projected area and a [100] face ratio of 90%.

The silver halide grains obtained as described above were warmed to a temperature of 60° C., added with 76 μmoles of sodium benzenesulfonate per mole of silver, and after 3 minutes, added with 71 μmoles of triethylthiourea. Then, the mixture was ripened for 100 minutes, and added with $5 \times 10^{-4}$ mole of 4-hydroxy-6-methyl-1,3,3a,7-tetrazaindene, and the temperature of the mixture was lowered to 40° C.

Thereafter, while the mixture was kept at a temperature of 40° C., the mixture was added with $12.8 \times 10^{-4}$ mole of Sensitizing dye A and $6.4 \times 10^{-3}$ mole of Compound B per mole of silver halide with stirring. After 20 minutes, the mixture was quenched to 30° C. to finish the preparation of Silver halide emulsion A.

2. Preparation of Organic Silver Salt Dispersion (Organic Silver Salt A)

87.6 kg of behenic acid (Edenor C22-85R, trade name, manufactured by Henkel Co.), 423 L of distilled water, 49.2 L of a 5 mol/L aqueous solution of NaOH and 120 L of tert-butanol were mixed and allowed to react with stirring at 75° C. for one hour to obtain a solution of sodium behenate.

Separately, 206.2 L of an aqueous solution containing 40.4 kg of silver nitrate was prepared and kept at 10° C. A mixture of 635 L of distilled water and 30 L of tert-butanol contained in a reaction vessel kept at 30° C. was added with the whole amount of the aforementioned sodium behenate solution and the whole amount of the aqueous silver nitrate solution at constant flow rates over the periods of 62 minutes and 10 seconds, and 60 minutes, respectively. In this case, they were added in such a manner that only the aqueous silver nitrate solution was added for 7 minutes and 20 seconds after starting the addition of the aqueous silver nitrate solution, and for 9 minutes 30 seconds after finishing the addition of the aqueous silver nitrate solution, only the sodium behenate solution was added. In this operation, the outside temperature was controlled so that the temperature in the reaction vessel should become 30° C. and the liquid temperature should not be raised. The piping of the addition system for the sodium behenate solution was maintained by steam trace and the steam amount was controlled such that the liquid temperature at the outlet orifice of the addition nozzle should be 75° C. The piping of the addition system for the aqueous silver nitrate solution was maintained by circulating cold water outside a double pipe. The addition position of the sodium behenate solution and the addition position of the aqueous silver nitrate solution were arranged symmetrically with respect to the stirring axis as the center, and the positions are controlled at heights for not contacting with the reaction liquid.

After finishing the addition of the sodium behenate solution, the mixture was left with stirring for 20 minutes at the same temperature and then the temperature was decreased to 25° C. Thereafter, the solid content was recovered by a suction filtration and the solid content was washed with water until electric conductivity of the filtrate became 30 $\mu$S/cm. The solid content obtained as described above was stored as a wet cake without being dried.

When the shape of the obtained silver behenate grains was evaluated by an electron microscopic photography, the grains were scaly crystals having a mean diameter of projected area of 0.52 $\mu$m, a mean grain thickness of 0.14 $\mu$m, and a variation coefficient of 15% for mean diameter as spheres.

Then, a dispersion of silver behenate was prepared as follows. To the wet cake corresponding to 100 g of the dry solid content was added with 7.4 g of polyvinyl alcohol (PVA-217, trade name, average polymerization degree: about 1700) and water to make the total amount 385 g, and the mixture was pre-dispersed by a homomixer. Then, the pre-dispersed stock dispersion was treated three times by using a dispersing machine (Microfluidizer-M-110S-EH; trade name, manufactured by Microfluidex International Corporation, using G10Z interaction chamber) with a pressure controlled to be 1750 kg/cm$^2$ to obtain a silver behenate dispersion. During the cooling operation, a desired dispersion temperature was achieved by providing coiled heat exchangers fixed before and after the interaction chamber and controlling the temperature of the refrigerant.

The silver behenate grains contained in the silver behenate dispersion obtained as described above were grains having a volume weight mean diameter of 0.52 $\mu$m and a coefficient of variation of 15%. The measurement of the grain size was carried out by using Master Sizer X manufactured by Malvern Instruments Ltd. When the grains were evaluated by an electron microscopic photography, the ratio of the long side to the short side was 1.5, the grain thickness was 0.14 $\mu$m and a mean aspect ratio (ratio of circular diameter of projected area of grain and grain thickness) was 5.1.

3. Preparation of Dispersion of Solid Microparticles of Reducing Agent: 1,1-bis(2-hydroxy-3,5-dimethylphenyl)-3,5,5-trimethylhexane 25 g of 1,1-bis(2-hydroxy-3,5-dimethylphenyl)-3,5,5-trimethylhexane was added with 25 g of a 20% by weight aqueous solution of MP polymer (MP-203, manufactured by KURARAY CO., LTD.), 0.1 g of Safinol 104E manufactured by Nisshin Kagaku K.K., 2 g of methanol and 48 ml of water and the mixture was stirred sufficiently to form a slurry, which was left for 3 hours as slurry. Then, 360 g of zirconia beads having a mean diameter of 1 mm were placed in a vessel together with the slurry and the slurry was dispersed by a dispersing machine (¼ G Sand Grinder Mill; manufactured by Imex Co.) for 3 hours to prepare a dispersion of reducing agent solid microparticles. As for the particle sizes, 80% of the particles had a particle size of 0.3 $\mu$m to 1.0 $\mu$m.

4. Preparation of Solid Microparticle Dispersion of Compound of Formula (1) According to the Invention 30 g of each of the compounds of the formula (1) shown in Table 2 was added with 4 g of MP polymer (MP-203 manufactured by KURARAY CO., LTD.), 0.25 g of Compound C and 66 g of water and the mixture was stirred sufficiently to form a slurry. Thereafter, 200 g of zirconia silicate beads having a diameter of 0.5 mm were placed in a vessel together with the slurry and the slurry was dispersed by a dispersing machine (¹⁄₁₆ G Sand Grinder Mill; manufactured by Imex Co.) for 5 hours to prepare a solid microparticle dispersion. In the particles, 80% by weight of the particles had a diameter of 0.3 $\mu$m to 1.0 $\mu$m. Each of Comparative Compounds P-1 to P-5 was also dispersed in the same manner as above.

5. Preparation of Solid Microparticle Dispersion of Ultrahigh Contrast Agent B 10 g of Ultrahigh contrast agent B was added with 2.5 g of polyvinyl alcohol (PVA-217, manufactured by KURARAY CO., LTD.) and 87.5 g of water and the mixture was stirred sufficiently to form a slurry, which was left for 3 hour as slurry. Thereafter, 240 g of zirconia beads having a diameter of 0.5 mm were placed in a vessel together with the slurry and the slurry was dispersed by a dispersing machine (¼ G Sand Grinder Mill; manufactured by Imex Co.) for 10 hours to prepare a solid microparticle dispersion. In the particles, 80% by weight of the particles had a size of 0.1 $\mu$m to 1.0 $\mu$m, and the mean particle size was 0.5 $\mu$m.

6. Preparation of Solid Microparticle Dispersion of Compound Z 30 g of Compound Z was added with 3 g of MP polymer (MP-203, manufactured by KURARAY CO. LTD.) and 87 ml of water, and the mixture was stirred sufficiently to form a slurry, which was left for 3 hours as slurry. Thereafter, by following the same procedure as the preparation of the aforementioned solid microparticle dispersion of the reducing agent, a solid microparticle dispersion of Compound Z was prepared. In the particles, 80% by weight of the particles had a size of 0.3 $\mu$m to 1.0 $\mu$m.

7. Preparation of Coating Solution for Emulsion Layer

To 1 mole of silver of the organic acid silver salt microcrystal dispersion prepared as described above were added the following binder, materials, Silver halide emulsion A and water to provide a coating solution for emulsion layer.

| | |
|---|---:|
| Binder; Laxster 3307B (made by DAINIPPON INK AND CHEMICALS, INC.; SBR latex, glass transition temperature: 17° C.) | 500 g as solid content |
| 1,1-Bis(2-hydroxy-3,5-dimethylphenyl-3,5,6-trimethylhexane | 149 g as solid content |

-continued

| Compound of the formula (1) | Type and amount (mole) shown in Table 2 |
|---|---|
| Ultrahigh contrast agent B | 15 g as solid content |
| Sodium ethylthiosulfonate | 0.15 g |
| 4-Methylbenzotriazole | 1.04 g |
| Polyvinyl alcohol (PVA-235, made by KURARAY CO. LTD.) | 10.8 g |
| 6-Isopropylphthalzine | 15.0 g |
| Sodium dihydrogen-orthophsophsate.dihydride | 0.37 g |
| Compound Z | 9.7 g as solid content |
| Dye A | Amount giving an optical density of 0.3 at 783 nm (about 0.37 g) |
| Silver halide emulsion A | 0.06 mole as Ag |

8. Preparation of Coating Solution for Lower Protective Layer of Emulsion Layer Surface 956 g of a polymer latex solution of methyl methacrylate/styrene/2-ethylhexyl acrylate/2-hydroxyethyl methacrylate/acrylic acid copolymer=58.9/8.6/25.4/5.1/2 (% by weight) having a particle size of 120 nm (glass transition temperature: 57° C. solid content concentration: 21.5% by weight, containing Compound D as film-forming aid in an amount of 15% by weight relative to the solid content of the latex) was added with water, and then added with 1.62 g of Compound E, 3.15 g of Compound S, 1.98 g of a matting agent (polystyrene particles, mean particle size: 7 μm), 23.6 g of polyvinyl alcohol (PVA-235, manufactured by KURARAY CO., LTD.) and water to prepare a coating solution.

9. Preparation of Coating Solution for Upper Protective Layer of Emulsion Layer Surface 630 g of a polymer latex containing copolymer of methyl methacrylate/styrene/2-ethylhexyl acrylate/2-hydroxyethyl methacrylate/acrylic acid=58.9/8.6/25.4/5.1/2 (% by weight) (glass transition temperature: 54° C., solid content: 21.5% by weight, mean particle diameter: 70 nm, containing Compound D as a film-forming aid in an amount of 15% by weight as to solid content of the latex) was added with $H_2O$, 6.30 g of 30% by weight solution of carnauba wax (Cellosol 524, Chukyo Yushi Co., Ltd.), 0.72 g of Compound E, 7.95 g of Compound F, 0.09 g of Compound S, 1.18 g of a matting agent (polystyrene particles, mean diameter: 7 μm) and 8.30 g of polyvinyl alcohol (PVA-235, Kuraray Co., Ltd.) and further added with $H_2O$ to form a coating solution.

10. Preparation of PET Support Having Backing Layer/undercoat Layer (1) Support

Using terephthalic acid and ethylene glycol, PET having an intrinsic viscosity IV of 0.66 (measured in phenol/tetrachloroethane=6/4 (weight ratio) at 25° C.) was obtained in a conventional manner. The PET was pelletized, and the pellets were dried at 130° C. for 4 hours, melted at 300° C., extruded from a T-die, and quenched to prepare an unstretched film having such a thickness that the film thickness after thermal fixation should become 120 μm.

The film was stretched along the longitudinal direction by 3.3 times using rollers having different peripheral speeds and then stretched along the transverse direction by 4.5 times using a tenter. In this case, the temperatures were 121° C. and 130° C., respectively. Thereafter, the film was subjected to thermal fixation at 240° C. for 20 seconds and relaxed by 4% along the transverse direction at the same temperature. Then, after chucks of the tenter were released, the both edges of the film were knurled, and the film was rolled up at 4.8 $kg/cm^2$ to provide a roll of the film having a width of 2.4 m, length of 3500 m and thickness of 120 μm.

(2) Undercoat layer (a):

| | |
|---|---|
| Polymer latex (1) (core shell type latex comprising 90% by weight of core and 10% by weight of shell, core: vinylidene chloride/methyl acrylate/methyl methacrylate/acrylonitrile/acrylic acid = 93/3/3/0.9/0.1 (% by weight), shell: vinylidene chloride/methyl acrylate/methyl methacrylate/acrylonitrile/acrylic acid = 88/3/3/3/3 (% by weight), weight average molecular weight; 38000) | 3.0 $g/m^2$ as solid content |
| 2,4-Dichloro-6-hydroxy-s-triazine | 23 $mg/m^2$ |
| Matting agent (polystyrene, mean diameter; 2.4 μm) | 1.5 $mg/m^2$ |
| (3) Undercoat layer (b) | |
| Deionized gelatin ($Ca^{2+}$ content; 0.6 ppm, jelly strength; 230 g) | 50 $mg/m^2$ |
| (4) Electroconductive layer | |
| Julimer ET-410 (Nihon Junyaku Co., Ltd.) | 96 $mg/m^2$ |
| Alkali-treated gelatin (molecular weight; about 10000, $Ca^{2+}$ content; 30 ppm) | 42 $mg/m^2$ |
| Deionized gelatin ($Ca^{2+}$ content; 0.6 ppm) | 8 $mg/m^2$ |
| Compound A | 0.2 $mg/m^2$ |
| Polyoxyethylene phenyl ether | 10 $mg/m^2$ |
| Sumitex Resin M-3 (water-soluble melamine resin, Sumitomo Chemical Co., Ltd.) | 18 $mg/m^2$ |
| Dye A | Amount giving optical density of 1.2 at 783 nm |
| $SnO_2$/Sb (weight ratio: 9/1, acicular grains, long axis/short axis = 20–30, Ishihara Sangyo Kaisha, Ltd.) | 160 $mg/m^2$ |
| Matting agent (Polymethyl methacrylate, mean particle size: 5 μm) | 7 $mg/m^2$ |
| (5) Protective layer | |
| Polymer latex (2) (copolymer of methyl methacrylate/styrene/2-ethylhexyl acrylate/2-hydroxyethyl methacrylate/acrylic acid = 59/9/26/5/1 (% by weight)) | 1000 $mg/m^2$ as solid content |
| Polystyrenesulfonate (molecular weight: 1000–5000) | 2.6 $mg/m^2$ |
| Cellosol 524 (Chukyo Yushi Co., Ltd.) | 25 $mg/m^2$ |
| Sumitex Resin M-3 (water-soluble melamine compound, Sumitomo Chemical Co., Ltd.) | 218 $mg/m^2$ |

(6) Preparation of PET Support with Backing Layer and Undercoat Layer

Undercoat layer (a) and Undercoat layer (b) were applied successively on both sides of the support (base), and each dried at 180° C. for 4 minutes. Then, an electroconductive layer and a protective layer are successively applied to one side provided with Undercoat layer (a) and Undercoat layer (b), and each dried at 180° C. for 4 minutes to prepare a PET support having backing layers and undercoat layers. The dry thickness of Undercoat layer (a) was 2.0 μm.

(7) Heat Treatment During Transportation (7-1) Heat Treatment

The PET support with backing layers and undercoat layers prepared as described above was introduced into a heat treatment zone having a total length of 200 m set at 160° C., and transported at a tension of 3 $kg/cm^2$ and a transportation speed of 20 m/minute.

(7-2) Post-heat Treatment

Following the aforementioned heat treatment, the support was passed through a zone at 40° C. for 15 seconds for post-heat treatment, and rolled up. The rolling up tension for this operation was 10 kg/cm$^2$.

11. Preparation of Thermally Processed Image Recording Material

On the undercoat layers of the aforementioned PET support coated with Undercoat layer (a) and Undercoat layer (b), the coating solution for emulsion layer was coated so that the coated silver amount should become 1.6 g/m$^2$. Further, the coating solution for lower protective layer for emulsion surface was coated on the emulsion layer simultaneously with the coating solution for emulsion layer as laminated layers, so that the coated solid content of the polymer latex should be 1.31 g/m$^2{}_1$. Then, the coating solution for upper protective layer for emulsion surface was coated on the coated layer, so that the coated solid content of the polymer latex should be 3.02 g/m$^2$ to obtain a thermally processed image recording material. The film surface pH of the obtained thermally processed image recording material on the image-forming layer side was 4.9, and the Beck's smoothness was 660 seconds. As for the opposite surface, the film surface pH was 5.9 and the Beck's smoothness was 560 seconds.

12. Evaluation of Photographic Performance (Light Exposure)

The obtained thermally processed image recording material was light exposed for 2×10$^{-8}$ seconds by using a laser light-exposure apparatus of single channel cylindrical inner surface type provided with a semiconductor laser with a beam diameter (½ of FWHM of beam intensity) of 12.56 μm, laser output of 50 mw and output wavelength of 783 nm. The exposure time was adjusted by controlling the mirror revolution number, and exposure was adjusted by changing output. The overlap coefficient of the light exposure was 0.449.

(Heat Development)

Each light-exposed thermally processed image recording material was heat-developed by using a heat-developing apparatus as shown in FIG. 1. The roller surface material of the heat development section was composed of silicone rubber, and the flat surface consisted of Teflon non-woven fabric. The heat development was performed at a transportation linear speed of 20 mm/second and a temperature of 90–110° C. in the preheating section for 15 seconds (driving units of the preheating section and the heat development section were independent from each other, and speed difference as to the heat development section was adjusted to −0.5% to −1%), and 120° C. for 20 seconds in the heat development section, and for 15 seconds in the gradual cooling section. The temperature precision as for the transverse direction was ±1° C.

(Evaluation of Photographic Performance)

The evaluation of the image obtained was performed by using a Macbeth TD904 densitometer (visible density). The measurement results were evaluated as Dmin, sensitivity (evaluated by a relative value of a reciprocal of a ratio of exposure amounts giving a density higher than Dmin by 1.0, and the sensitivity of the thermally processed image recording material of Experiment No. 1 shown in Table 1 below was defined as 100), Dmax, and gradation (contrast) (fresh photographic properties). The contrast was expressed by a gradient of a straight line connecting the points at the densities from which the value for Dmin was subtracted, 0.3 and 1.5, with the abscissa being a logarithm of the exposure amount.

As for the evaluation of image storage stability, Image storage stability 1 shows the change of the photographic properties after storing the thermally processed image recording materials after heat development in the dark for 24 hours at a temperature of 60° C. and relative humidity of 50%, and Image storage stability 2 shows the change of the photographic properties after storing them for 24 hours under the light irradiation of 10,000 luces at a temperature of 40° C. and relative humidity of 50%.

TABLE 2

| Ex. No. | Compound of formula (1) | Added amount (mol/mol-Ag) | Fresh photographic property | | | | Image storage stability-1 (stored in dark, 60°, 50%) | | Image storage stability-2 (stored in light, 40° C., 50%) | | Note |
|---|---|---|---|---|---|---|---|---|---|---|---|
| | | | Dmin | Sensitivity | Gradation | Dmax | Dmin | Dmax | Dmin | Dmax | |
| 1 | D-1 | 0.08 | 0.06 | 100 | 18.4 | 4.0 | 0.08 | 3.9 | 0.07 | 4.0 | Example |
| 2 | D-2 | 0.08 | 0.06 | 103 | 20.8 | 4.1 | 0.08 | 4.0 | 0.08 | 4.1 | Example |
| 3 | D-3 | 0.08 | 0.06 | 100 | 19.9 | 4.1 | 0.08 | 4.0 | 0.07 | 4.0 | Example |
| 4 | D-4 | 0.08 | 0.06 | 98 | 18.3 | 4.1 | 0.08 | 4.0 | 0.07 | 4.1 | Example |
| 5 | D-14 | 0.08 | 0.06 | 101 | 19.9 | 4.0 | 0.09 | 3.8 | 0.09 | 4.0 | Example |
| 6 | P-1 | 0.08 | 0.06 | 100 | 20.4 | 4.0 | 0.34 | 3.8 | 0.25 | 3.8 | Comparative Example |
| 7 | P-2 | 0.08 | 0.07 | 97 | 20.5 | 4.1 | 0.38 | 3.4 | 0.19 | 3.7 | Comparative Example |
| 8 | P-3 | 0.08 | 0.06 | 99 | 19.3 | 4.1 | 0.43 | 3.8 | 0.22 | 3.8 | Comparative Example |
| 9 | P-4 | 0.08 | 0.10 | 105 | 21.3 | 4.1 | 0.42 | 3.7 | 0.23 | 3.8 | Comparative Example |
| 10 | P-5 | 0.08 | 0.07 | 100 | 18.5 | 4.0 | 0.35 | 3.8 | 0.22 | 3.6 | Comparative Example |

As seen from the results shown in Table 2, when the compounds of the invention were used for the thermally processed image recording materials, good photographic performance (sensitivity, fog, gradation) and good image storage stability could be obtained.

What is claimed is:

1. A polyhalogenomethylsulfonyl compound represented by the following formula (1), or salts thereof, or hydrates or solvates thereof:

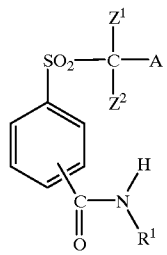
(1)

wherein $Z^1$ and $Z^2$ each independently represents a halogen atom; A represents a hydrogen atom or a halogen atom; and $R^1$ represents an alkyl group having from 2 to 12 carbon atoms, which may have one or more substituents, an alkenyl group having from 2 to 12 carbon atoms, which may have one or more substituents, or an alkinyl group having from 2 to 12 carbon atoms, which may have one or more-substituents.

2. The polyhalogenomethylsulfonyl compound according to claim 1, or salts thereof, or hydrates or solvates thereof, wherein $R^1$ is an unsubstituted alkyl group having from 2 to 12 carbon atoms, an unsubstituted alkenyl group having from 2 to 12 carbon atoms, or an unsubstituted alkinyl group having from 2 to 12 carbon atoms.

3. The polyhalogenomethylsulfonyl compound according to claim 1, or salts thereof, or hydrates or solvates thereof, wherein $R^1$ is an unsubstituted alkyl group having from 3 to 5 carbon atoms, an unsubstituted alkenyl group having from 3 to 5 carbon atoms, or an unsubstituted alkinyl group having from 3 to 5 carbon atoms.

4. The polyhalogenomethylsulfonyl compound according to claim 1, or salts thereof, or hydrates or solvates thereof, wherein the substituent which may exist on the alkyl group, the alkenyl group, or the alkinyl group represented by $R^1$ is one or more substituents selected from the group consisting of a halogen atom; an alkoxy group; a nitro group: an amino group which may be substituted by an alkyl group; an alkoxycarbonyl group; an acylthio group; a silyl group; an alkylthio group; and a heterocyclic group.

5. The polyhalogenomethylsulfonyl compound according to claim 1, or salts thereof, or hydrates or solvates thereof, wherein $Z^1$ and $Z^2$ each is a bromine atom.

6. The polyhalogenomethylsulfonyl compound according to claim 1, or salts thereof, or hydrates or solvates thereof, wherein A is a hydrogen atom or a bromine atom.

7. The polyhalogenomethylsulfonyl compound according to claim 1, or salts thereof, or hydrates or solvates thereof, wherein $Z^1$ and $Z^2$ each is a bromine atom, and A is a hydrogen atom or a bromine atom.

8. The polyhalogenomethylsulfonyl compound according to claim 1, or salts thereof, or hydrates or solvates thereof, wherein —$CONHR^1$ exists at the meta-position to –$SO_2C(Z^1)(Z^2)A$.

* * * * *